(12) United States Patent
Chauhan et al.

(10) Patent No.: US 11,931,321 B2
(45) Date of Patent: *Mar. 19, 2024

(54) COMPOSITIONS COMPRISING A DENDRIMER-RESVERATROL COMPLEX AND METHODS FOR MAKING AND USING THE SAME

(71) Applicant: Concordia University, Mequon, WI (US)

(72) Inventors: Abhay Singh Chauhan, Milwaukee, WI (US); Eric Andrew Newenhouse, Cedarburg, WI (US); Armin Henry Gerhardt, Mettawa, IL (US)

(73) Assignee: Concordia University, Mequon, WI (US)

( * ) Notice: Subject to any disclaimer, the term of this patent is extended or adjusted under 35 U.S.C. 154(b) by 282 days.

This patent is subject to a terminal disclaimer.

(21) Appl. No.: 17/325,088

(22) Filed: May 19, 2021

(65) Prior Publication Data

US 2021/0267910 A1 Sep. 2, 2021

Related U.S. Application Data

(63) Continuation of application No. 16/522,459, filed on Jul. 25, 2019, now Pat. No. 11,110,068, which is a continuation of application No. 15/832,059, filed on Dec. 5, 2017, now Pat. No. 10,406,119, which is a continuation of application No. 14/913,272, filed as application No. PCT/US2014/052105 on Aug. 21, 2014, now Pat. No. 9,855,223.

(60) Provisional application No. 61/959,344, filed on Aug. 21, 2013.

(51) Int. Cl.
| | | |
|---|---|---|
| *A61K 31/05* | (2006.01) | |
| *A61K 9/00* | (2006.01) | |
| *A61K 9/06* | (2006.01) | |
| *A61K 9/10* | (2006.01) | |
| *A61K 9/51* | (2006.01) | |
| *A61K 45/06* | (2006.01) | |
| *A61K 47/59* | (2017.01) | |

(52) U.S. Cl.
CPC ............ *A61K 31/05* (2013.01); *A61K 9/0014* (2013.01); *A61K 9/0053* (2013.01); *A61K 9/06* (2013.01); *A61K 9/10* (2013.01); *A61K 9/5146* (2013.01); *A61K 45/06* (2013.01); *A61K 47/595* (2017.08)

(58) Field of Classification Search
CPC .................................................... A61K 31/05
See application file for complete search history.

(56) References Cited

U.S. PATENT DOCUMENTS

| | | | | |
|---|---|---|---|---|
| 1,110,068 | A * | 9/1914 | Cauhan ................ | H05K 1/0228 |
| | | | | 174/45 R |
| 6,878,751 | B1 | 4/2005 | Donnelly | |
| 9,855,223 | B2 * | 1/2018 | Chauhan ................. | A61K 9/10 |
| 10,406,119 | B2 * | 9/2019 | Chauhan .............. | A61K 9/5146 |
| 2002/0173472 | A1 | 11/2002 | Pezzuto et al. | |
| 2003/0104040 | A1 | 6/2003 | Kirby et al. | |
| 2009/0068132 | A1 | 3/2009 | Bratescu | |
| 2010/0204179 | A1 | 8/2010 | Souto | |
| 2010/0297199 | A1 | 11/2010 | Duan et al. | |
| 2013/0023590 | A1 | 1/2013 | Giosan | |
| 2013/0129809 | A1 | 5/2013 | Srivastava et al. | |

OTHER PUBLICATIONS

Canadian Patent Office action for Application No. 2,921,937 dated Sep. 9, 2022 (3 pages).
"Resveratrol (Exhibit A)", Sigma-Aldrich, Retrieved from the Internet: URL:http://www.sigmaaldrich.com/catalog/product/sigma/r5010?lang=en&region=US [retrieved on Jun. 27, 2017].
"Appendix VIII P Quantification of Residual Solvent," Pharmacopoeia, People's Republic of China, 2010 (2nd Ed.), Dec. 2010, 61-65 (6 pages).
Abderrezak et al. "Dendrimers Bind Antioxidant Polyphenols and cisPlatin drug", PLOS ONE, 7(3), article e33102 (2012), p. 1, 3-5.
Abderrezak et al. , "Dendrimers Bind Antioxidant Polyphenols and cisPlatin drug," PLoS One, 2012, 7(3):e33101: 1-12.
Chen et al., "Transdermal delivery of nonsteroidal anti-inflamatory drugs mediated by polyamidoamine (PAMAM) dendrimers," Journal of pharmaceutical sciences, 2007, 9(3):595-602.
Chinese Patent Office Action for Application No. 201480057872.X dated Dec. 19, 2018 ( pages, Need Engl Translation). Chinese Patent Office Action for Application No. 201480057872.X dated Mar. 19, 2018 (8 pages).
Chinese Patent Office Action for Application No. 201480057872.X dated May 22, 2019.
EP14837985.2 Extended European Search Report dated Apr. 19, 2017 (6 pages).
European Patent Office Action for Application No. 14837985.2 dated Mar. 4, 2019 (5 pages).
European Patent Office Action for Application No. 14837985.2 dated Mar. 7, 2018 (6 pages).
First Office Action from the State Intellectual Property Office of China for Application No. 201480057872.X dated Jun. 16, 2017 (13 pages).
PCT/US2014/052105 International Search Report dated Nov. 6, 2014.
PCT/US2014/052105 Written Opinion dated Nov. 6, 2014.

(Continued)

*Primary Examiner* — Rei Tsang Shiao
(74) *Attorney, Agent, or Firm* — Michael Best & Friedrich LLP

(57) ABSTRACT

Compositions and pharmaceutical compositions including a dendrimer-resveratrol complex and methods for making and using the compositions are described herein. Methods of treating cancer, cardiovascular disease, cardiac failure, diabetes, Alzheimer's disease, Parkinson's disease and other brain diseases, fatty liver disease, obesity, cataracts, osteoporosis, muscle wasting, sleep disorders, acoustic trauma, inflammatory disease, psoriasis, arthritis, colitis, aging, viral disease, reproductive disease, and skin conditions or disorders including administering a therapeutically effective amount of the compositions to a subject in need are also provided. The compositions may be topically applied to skin or mucous membranes.

21 Claims, 7 Drawing Sheets

(56) References Cited

OTHER PUBLICATIONS

Sakthivel et al., "Synthesis and Physicochemical Properties of Lipophilic Polyamide Dendrimers," Pharm Res., 1988, 15(5): 776-82.
Twyman et al., "The Synthesis of Water Soluble Dendrimers, and their Application as Possible Drug Delivery Systems", Tetrahedron Letters, 1999, vol. 40, No. 9, pp. 1743-1746.
United States Patent Office Action for U.S. Appl. No. 15/832,059 dated Jan. 3, 2019 (6 pages).
United States Patent Office Action for U.S. Appl. No. 15/832,059 dated Jun. 4, 2018 (12 pages).
United States Patent Office Notice of Allowance for U.S. Appl. No. 15/832,059 dated Apr. 24, 2019 (9 pages).
Venuganti et al., "Structure-skin permeability relationship of dendrimers," Pharm. Res., 2011, 28(9):22246-60(Abstract only).
Zeng et al., "The Advantages of Dendrimers as Drug Carriers," Biomedical Biomimetic Polymer Material, ISBN 978-7-5623-3332-6, published Oct. 2010, 188-193 (7 pages).
European Patent Office Action for Application No. 14837985.2 dated Apr. 8, 2020 (5 pages).
Chinese Patent Office Action for Application No. 201480057872.X dated Aug. 20, 2020 (23 pages, English translation included).
Canadian Patent Office Action for Application No. 2,921,937 dated Aug. 28, 2020 (4 pages).
Canadian Patent Office Action for Application No. 2,921,937 dated Apr. 20, 2021 (3 pages).
Chinese Patent Office Notice of Reexamination for Application No. 201480057872.X dated Mar. 1, 2021 (22 pages including statement of relevance).
Canadian Patent Office Action for Application No. 2,921,937 dated Dec. 17, 2021 (3 pages).

* cited by examiner

FIG. 4

COMPOSITIONS COMPRISING A DENDRIMER-RESVERATROL COMPLEX AND METHODS FOR MAKING AND USING THE SAME

CROSS-REFERENCE TO RELATED APPLICATION

This application is a continuation of U.S. patent application Ser. No. 16/522,459, filed Jul. 25, 2019, which is a continuation of U.S. patent application Ser. No. 15/832,059, filed Dec. 5, 2017, which is a continuation of U.S. patent application Ser. No. 14/913,272, filed Feb. 19, 2016, which is the United States national stage entry, under 35 U.S.C. § 371, of International Application No. PCT/US2014/052105, filed Aug. 21, 2014, which claims priority to U.S. Provisional Patent Application No. 61/959,344, filed on Aug. 21, 2013, the entire contents of each of which are hereby incorporated by reference.

BACKGROUND

Resveratrol (3,4',5-trihydroxystilbene) (FIG. 1) is a naturally occurring phytoalexin produced by a variety of plants in response to stress. Resveratrol has wide pharmacological applications and is being investigated for the treatment of numerous conditions and/or disorders, such as cancer, cardiovascular disease, cardiac failure, type 2 diabetes, Alzheimer's disease, Parkinson's disease, fatty liver disease, cataracts, osteoporosis, muscle wasting, sleep disorders, acoustic trauma and inflammatory diseases such as psoriasis, arthritis and colitis (inflammatory bowel disease).

In spite of its great pharmacological potential, resveratrol lags as a pharmacological agent due its suboptimal pharmacokinetic profile. Resveratrol has low aqueous solubility (15-40 ng/mL), poor metabolic stability, and poor photostability. These properties contribute greatly to its poor pharmacokinetic properties, such as short half-life (~8-14 min) and low oral bioavailability.

Accordingly, there is a need for effective methods of formulating resveratrol.

SUMMARY

In one aspect, disclosed is a composition comprising a dendrimer-resveratrol complex, the composition being essentially free of organic solvent.

In another aspect, disclosed is a semi-solid composition comprising a dendrimer-resveratrol complex.

In certain embodiments, the semi-solid composition is a cream, ointment, paste or gel for topical application to skin or mucous membranes.

In another aspect, disclosed is a composition comprising a dendrimer-resveratrol complex and water.

In certain embodiments, the composition comprises water.

In certain embodiments, the pH of the composition is about 7.

In certain embodiments, at least 95%, by weight, of the resveratrol in the composition is associated with the dendrimer.

In certain embodiments, the aqueous solubility of the resveratrol associated with the dendrimer is at least 40 times greater than the aqueous solubility of neat resveratrol, as measured at pH 7.

In certain embodiments, the concentration of resveratrol associated with the dendrimer is at least 0.003 mM, as measured according to the total volume of the composition.

In certain embodiments, the aqueous solubility of the resveratrol associated with the dendrimer is at least 100 times greater than the aqueous solubility of neat resveratrol, as measured at pH 7.

In certain embodiments, the concentration of resveratrol associated with the dendrimer is at least 0.01 mM, as measured according to the total volume of the composition.

In certain embodiments, the aqueous solubility of the resveratrol associated with the dendrimer is at least 40 times greater than the aqueous solubility of neat resveratrol, as measured at pH 2.5.

In certain embodiments, the time to dissolution of the composition in simulated intestinal fluid is less than 30 minutes.

In certain embodiments, the time to dissolution of the composition in simulated gastric fluid is less than 30 minutes.

In certain embodiments, the resveratrol associated with the dendrimer degrades less than 10% after 4 days at ambient temperature.

In certain embodiments, at least 50%, by weight, of the resveratrol associated with dendrimer permeates the skin in 20 minutes or less in a transdermal permeation study utilizing Franz Diffusion Cells and rat skin samples.

In certain embodiments, the composition comprises about 1.0 mM dendrimer or less.

In certain embodiments, the composition comprises about 0.40 mM dendrimer or less.

In certain embodiments, the composition is selected from the group consisting of: a composition comprising about 0.70 mM dendrimer and about 0.004 mM resveratrol, a composition comprising about 0.70 mM dendrimer and about 0.011 mM resveratrol, a composition comprising about 0.07 mM dendrimer and about 0.004 mM resveratrol, and a composition comprising about 0.07 mM dendrimer and about 0.005 mM resveratrol;

In certain embodiments, the dendrimer is poly(amidoamine) (PAMAM), poly(propyleneimine) (PPI), poly(lysine), poly(glycerol) or a hyperbranched structure; wherein the hyperbranched structure is selected from the group consisting of dendrigrafts, polyesters, polyamides, and polyalcohols.

In certain embodiments, the dendrimer is a generation 0 to generation 10 dendrimer.

In certain embodiments, the dendrimer surface groups are amine, hydroxyl, carboxylate, pyrrolidinone, cysteamine, or PEG.

In certain embodiments, the dendrimer core is ethylenediamine, diaminobutane, 1,12-diaminododecane, or cysteamine.

In certain embodiments, the dendrimer is a generation 4 PAMAM dendrimer comprising a diaminobutane core and amine surface groups.

In certain embodiments, the composition is a colloidal or coarse dispersion.

In certain embodiments, the composition further comprises at least one additional antioxidant.

In another aspect, disclosed is a pharmaceutical composition comprising a therapeutically effective amount of the composition and one or more pharmaceutically acceptable carriers.

In another aspect, disclosed is a method of preparing a composition comprising a dendrimer-resveratrol complex, the method comprising: mixing resveratrol, dendrimer, and solvent to form a mixture comprising a dendrimer-resveratrol complex; and filtering the mixture to form the composition.

In certain embodiments, the solvent is water.

In certain embodiments, the method further comprises: removing solvent after forming the mixture of the dendrimer-resveratrol complex to form a solid mixture; and adding water to the solid mixture.

In certain embodiments, the solvent is a mixture of water and a $C_1$-$C_4$ alcohol, wherein the solvent comprises less than 50%, by volume, the $C_1$-$C_4$ alcohol.

In certain embodiments, the solvent comprises about 5% to about 20%, by volume, the $C_1$-$C_4$ alcohol.

In certain embodiments, the solvent comprises about 10%, by volume, the $C_1$-$C_4$ alcohol.

In certain embodiments, the $C_1$-$C_4$ alcohol is methanol.

In certain embodiments, the pH of the composition is about 7.

In certain embodiments, at least 95%, by weight, of the resveratrol in the composition is associated with the dendrimer.

In certain embodiments, the aqueous solubility of the resveratrol associated with the dendrimer is at least 40 times greater than the aqueous solubility of neat resveratrol, as measured at pH 7.

In certain embodiments, the concentration of resveratrol associated with the dendrimer is at least 0.003 mM, as measured according to the total volume of the composition.

In certain embodiments, the aqueous solubility of the resveratrol associated with the dendrimer is at least 100 times greater than the aqueous solubility of neat resveratrol, as measured at pH 7.

In certain embodiments, the concentration of resveratrol associated with the dendrimer is at least 0.01 mM, as measured according to the total volume of the composition.

In certain embodiments, the aqueous solubility of the resveratrol associated with the dendrimer is at least 40 times greater than the aqueous solubility of neat resveratrol, as measured at pH 2.5.

In certain embodiments, the time to dissolution of the composition in simulated intestinal fluid is less than 30 minutes.

In certain embodiments, the time to dissolution of the composition in simulated gastric fluid is less than 30 minutes.

In certain embodiments, the resveratrol associated with dendrimer degrades less than 10% after 4 days at ambient temperature.

In certain embodiments, at least 50%, by weight, of the resveratrol associated with dendrimer permeates the skin in 20 minutes or less in a transdermal permeation study utilizing Franz Diffusion Cells and rat skin samples.

In certain embodiments, the composition comprises about 1.0 mM dendrimer or less.

In certain embodiments, the composition comprises about 0.40 mM dendrimer or less.

In certain embodiments, the composition is selected from the group consisting of: a composition comprising about 0.70 mM dendrimer and about 0.004 mM resveratrol; a composition comprising about 0.70 mM dendrimer and about 0.011 mM resveratrol; a composition comprising about 0.07 mM dendrimer and about 0.004 mM resveratrol; and a composition comprising about 0.07 mM dendrimer and about 0.005 mM resveratrol.

In certain embodiments, the dendrimer poly(amidoamine) (PAMAM), poly(propyleneimine) (PPI), poly(lysine), poly(glycerol), or a hyperbranched structure; wherein the hyperbranched structure is selected from the group consisting of dendrigrafts, polyesters, polyamides, and polyalcohols.

In certain embodiments, the dendrimer is a generation 4 PAMAM dendrimer comprising a diaminobutane core and amine surface groups.

In certain embodiments, the method further comprises drying the composition to solid form.

In certain embodiments, the method further comprises combining a therapeutically effective amount of the composition with one or more pharmaceutically acceptable carriers to form a pharmaceutical composition.

In certain embodiments, the method further comprises combining a therapeutically effective amount of the composition with an existing drug formulation to form a pharmaceutical composition.

In another aspect, disclosed is a method of treating cancer, cardiovascular disease, cardiac failure, diabetes, Alzheimer's disease, Parkinson's disease and other brain diseases, fatty liver disease, obesity, cataracts, osteoporosis, muscle wasting, sleep disorders, acoustic trauma, inflammatory disease, psoriasis, arthritis, colitis, aging, viral disease, reproductive disease, and skin conditions or disorders, the method comprising administering a therapeutically effective amount of the pharmaceutical composition to a subject in need thereof.

In certain embodiments, the pharmaceutical composition is topically administered to the skin or mucous membrane.

In certain embodiments, the pharmaceutical composition is orally administered.

In certain embodiments, the pharmaceutical composition is parenterally administered.

In another aspect, disclosed is a method of treating a skin condition or disorder, the method comprising topically administering to the skin or mucous membrane, a therapeutically effective amount of the pharmaceutical composition to a subject in need thereof.

In certain embodiments, the skin condition or disorder is skin cancer, hyperpigmentation, inflammation, burns, psoriasis, eczema, cellulitis, hives, dermatitits, acne, aging, UV light mediated aging, an inflammatory disorder, or a hyperproliferative disorder.

In another aspect, disclosed is a method of providing personal and/or cosmetic care, the method comprising topically administering to the skin or mucous membrane, a therapeutically effective amount of the pharmaceutical composition to a subject in need thereof.

In certain embodiments, the method further comprises administering an anti-aging product, a body lotion, a body treatment, a toner, a facial moisturizer, a facial treatment, makeup foundation, or any skin care product.

In another aspect, disclosed is a method of treating a skin condition or disorder, the method comprising topically administering to skin or mucous membrane of a subject in need thereof a therapeutically effective amount of a semi-solid composition comprising a dendrimer-resveratrol complex, wherein the concentration of dendrimer is less than 0.40 mM, wherein at least 50%, by weight, of the resveratrol associated with dendrimer permeates the skin in 20 minutes or less in a transdermal permeation study utilizing Franz Diffusion Cells and rat skin samples.

In another aspect, disclosed is a method of preparing a composition comprising a dendrimer-resveratrol complex, the method comprising: mixing resveratrol, dendrimer, water and essentially no organic solvent to form an aqueous mixture comprising a dendrimer-resveratrol complex; and filtering the mixture to form the composition comprising a dendrimer-resveratrol complex, the composition being essentially free of organic solvent, wherein the concentration of dendrimer is less than 0.40 mM, and the aqueous solubility of the resveratrol associated with the dendrimer being at least 40 times greater than the aqueous solubility of neat resveratrol, as measured at pH 7.

In another aspect, disclosed is a method of preparing a semi-solid topical composition comprising adding excipients to the semi-solid composition to form a semi-solid topical solution.

Other aspects and embodiments of the disclosure will become apparent in light of the following description.

BRIEF DESCRIPTION OF THE DRAWINGS

FIG. 4 is a series of graphs depicting the resveratrol concentration associated with 1% and 0.1% PAMAM G4-amine dendrimer-resveratrol formulations prepared by protocols 1 and 2 (upper); and the resveratrol concentration associated with 0.1% PAMAM G4-amine dendrimer-resveratrol formulation at pH 2.5 in comparison to neat resveratrol in water (lower).

DETAILED DESCRIPTION

Figure 1:
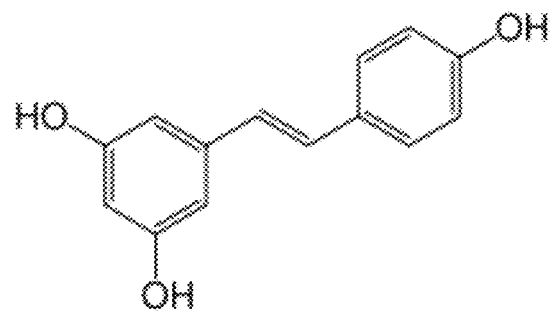
FIG. 1 is an illustration of the structure of resveratrol.

The present disclosure relates to compositions comprising a dendrimer-resveratrol complex. The compositions may further comprise optional additional components. The compositions may be in the form of a liquid (for example, a solution, such as an aqueous formulation), a semi-solid or a solid. The compositions may be prepared by mixing resveratrol and dendrimer in an appropriate solvent to promote the association of resveratrol and dendrimer and form a complex. The resulting compositions may increase the aqueous solubility and/or metabolic stability of resveratrol associated with the dendrimer, resulting in improved pharmacokinetic properties of resveratrol, such as half-life and oral bioavailability. Resveratrol associated with the dendrimer may also have improved transdermal permeability.

The composition can be used as a drug delivery system to deliver resveratrol to subjects in need in an efficient manner. The composition may be used to treat a variety of conditions and/or disorders, particularly skin conditions and disorders.

1. Definition of Terms

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present disclosure. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of" and "consisting essentially of," the embodiments or elements presented herein, whether explicitly set forth or not.

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

It is specifically understood that any numerical value recited herein (e.g., ranges) includes all values from the lower value to the upper value, i.e., all possible combinations of numerical values between the lowest value and the highest value enumerated are to be considered to be expressly stated in this application. For example, if a concentration range is stated as 1% to 50%, it is intended that values such as 2% to 40%, 10% to 30%, or 1% to 3%, etc., are expressly enumerated in this specification. These are only examples of what is specifically intended. With respect to amounts of components, all percentages are by weight, unless explicitly indicated otherwise.

Definitions of specific functional groups and chemical terms are described in more detail below. For purposes of this disclosure, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; March, *Advanced Organic Chemistry*, 5$^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3$^{rd}$ Edition, Cambridge University Press, Cambridge, 1987; the entire contents of each of which are incorporated herein by reference.

"Amine" refers to a group having the general structure $NR^1R^2R^3$, wherein N, le and $R^2$ are an amino group attached to $R^3$, which is an independent substituent.

"$C_1$-$C_4$ alcohol" refers to $C_1$-$C_4$ alkyl groups having one or more hydroxyl substituents. "$C_1$-$C_4$ alcohol" may be exemplified by methanol, ethanol, propanol, and butanol.

"Glycol" refers to a compound having vicinal hydroxyl groups (two hydroxyl groups on adjacent carbon atoms).

"Hydroxy" or "hydroxyl" refers to —OH. Alcohols contain hydroxy groups. Hydroxy groups may be free or protected.

"Solvent" refers to a substance that dissolves a solute (e.g., a chemically different liquid, solid or gas), resulting in a solution.

"Organic solvent" refers to a carbon-containing solvent. Examples of organic solvents include $C_1$-$C_4$ solvents, wherein the solvent has between 1 and 4 carbons. Examples of organic $C_1$-$C_4$ solvents include, but are not limited to, butanol, propanol, ethanol, methanol, dichloromethane, dichloroethane, diethyl ether, glycerine, ethylene glycol, and tetrahydrofuran.

"Compositions essentially free of organic solvent" refers to compositions comprising no organic solvent or a negligible amount of organic solvent. For example, a negligible amount of organic solvent may be less than about 1%, about 0.9%, about 0.8%, about 0.7%, about 0.6%, about 0.5%, about 0.4%, about 0.4%, about 0.3%, about 0.2%, about 0.1%, or about 0.05%, or about 0.01% of organic solvent by weight of the composition.

"Compositions essentially free of free resveratrol" refers to compositions comprising no free resveratrol or a negligible amount of free resveratrol. For example, a negligible amount of organic free resveratrol may be less than about 1%, about 0.9%, about 0.8%, about 0.7%, about 0.6%, about 0.5%, about 0.4%, about 0.4%, about 0.3%, about 0.2%, about 0.1%, or about 0.05%, or about 0.01% of free resveratrol by weight of the composition.

"Administering" refers to administration of the compositions as needed to achieve the desired effect.

"Excipient" includes physiologically compatible additives useful in preparation of a pharmaceutical composition. Examples of pharmaceutically or cosmetically acceptable carriers and excipients can for example be found in Remington Pharmaceutical Science, 16th Ed.

"Pharmaceutically acceptable carrier" means a carrier that is useful for the preparation of a pharmaceutical composition that is at least one of: generally compatible with the other ingredients of the composition, not deleterious to the recipient, and neither biologically nor otherwise undesirable. "A pharmaceutically acceptable carrier" includes both one and more than one carrier. Embodiments include carriers for topical, ocular, parenteral, intravenous, intraperitoneal intramuscular, sublingual, nasal and oral administration. "Pharmaceutically or cosmetically acceptable carrier" also includes agents for preparation of aqueous dispersions and sterile powders for injection or dispersions.

"Semi-solid" denotes a physical state that is neither solid nor liquid. Semi-solids (or quasi-solids) are similar to a solid in some respects, e.g., a semi-solid can support its own weight and hold its shape but also shares some properties of liquids, such as shape conformity to something applying pressure to it, or the ability to flow under pressure. Semi-solids are characterized by a three-dimensional structure that is sufficient to impart solid-like character to the undisturbed system but that is easily broken down and realigned under an applied force. Semi-solids have a rigidity and viscosity intermediate between a solid and a liquid.

"Therapeutically effective amount" refers to a dosage of a sufficient amount of the compositions of the disclosure to bring about a desired in vivo effect and treat disorders or conditions, at a reasonable benefit/risk ratio applicable to any medical treatment.

2. Compositions

The compositions comprise a dendrimer-resveratrol complex. The compositions may comprise one or more additional components. Compositions comprising dendrimer-resveratrol complexes may have improved properties relative to compositions comprising non-complexed resveratrol. The compositions may effectively improve one or more of the following properties of resveratrol: aqueous solubility, metabolic stability, photostability, chemical stability, transdermal permeability, and oral bioavailability. The composition may be in the form of a liquid, a solution, an aqueous solution, a dispersion, a suspension, a nanosuspension, a solid, a semi-solid, or a combination thereof. The dispersions may be colloidal or coarse. Colloidal and coarse dispersion include emulsions, suspensions, and nanosuspensions. The semi-solid composition may be a cream, ointment, paste or gel for topical application to skin or mucous membranes.

A. Dendrimer-Resveratrol Complex

The compositions comprise a dendrimer-resveratrol complex. In the dendrimer-resveratrol complex, resveratrol may be associated with the dendrimer. The dendrimer-resveratrol complex may include one or more molecules of resveratrol entrapped in the molecular framework of the dendrimer. The resveratrol may be associated with the dendrimer via hydrophobic interactions, hydrophilic interactions, electrostatic interactions, ionic interactions, hydrogen bonds, or a combination thereof.

B. Dendrimer

Figure 2:
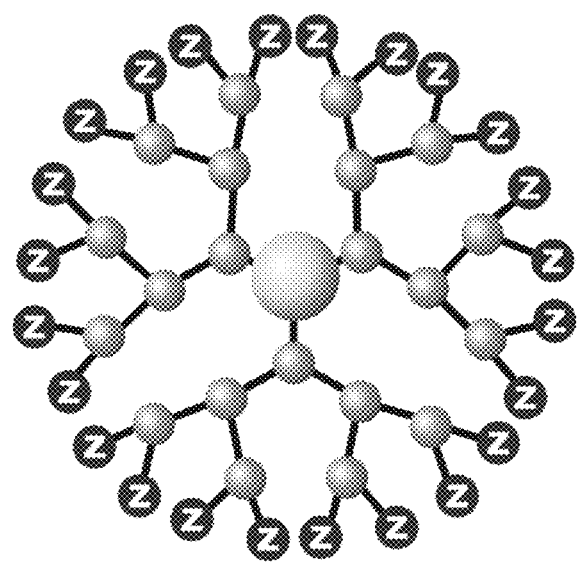
FIG. 2 is an illustration of the structure of a dendrimer.

Dendrimers are repetitively branched molecules. A dendrimer is typically symmetric around the core, and often adopts a spherical three-dimensional morphology (FIG. 2). Dendrimers are monodisperse and can be highly symmetric, spherical compounds.

The properties of dendrimers are dominated by the functional groups on the molecular surface, however, there are examples of dendrimers with internal functionality. Dendritic entrapment of functional molecules allows for the isolation of the active site, a structure that mimics that of active sites in biomaterials. Dendrimers may be water soluble by functionalizing their outer shell with charged species or other hydrophilic groups. Other controllable properties of dendrimers include toxicity, crystallinity, tectodendrimer formation, and chirality.

Dendrimers are also classified by generation, which refers to the number of repeated branching cycles that are performed during its synthesis. For example if a dendrimer is made by convergent synthesis, and the branching reactions are performed onto the core molecule three times, the resulting dendrimer is considered a third generation dendrimer. Each successive generation results in a dendrimer roughly twice the molecular weight of the previous generation. Higher generation dendrimers also have more exposed functional groups on the surface, which can later be used to customize the dendrimer for a given application.

The dendrimer of the composition may be a generation 0 to generation 10 dendrimer. The dendrimer may be a generation 0, generation 1, generation 2, generation 3, generation 4, generation 5, generation 6, generation 7, generation 8, generation 9, or generation 10 dendrimer.

Dendrimers have three major portions: a core, an inner shell, and an outer shell. A dendrimer can be synthesized to have different functionality in each of these portions to control properties such as solubility, thermal stability, and attachment of compounds for particular applications. Synthetic processes can also precisely control the size and number of branches on the dendrimer. There are two defined methods of dendrimer synthesis: divergent synthesis and convergent synthesis. However, because the actual reactions include many steps needed to protect the active site, it is difficult to synthesize dendrimers using either method. This makes dendrimers hard to make and very expensive to purchase.

Dendrimers provide an alternative route to create very well-defined nanostructures suitable for drug solubilization applications. The properties of dendrimer may be tailored to address therapeutic needs, which makes them useful carriers for small molecule drugs and biomolecules. The three main properties of dendrimers are (i) nanoscale container properties (i.e., entrapment of a drug), (ii) nano-scaffolding properties (i.e., surface adsorption or attachment of a drug), and (iii) biocompatibility. The composition comprising the dendrimer-resveratrol complex may be used in several routes of administration, including intravenous, oral, transdermal, and ocular. The use of dendrimers as drug carriers by entrapment of hydrophobic drugs is a potential method for delivering highly active pharmaceutical compounds that may not be in clinical use due to their limited water solubility and resulting suboptimal pharmacokinetics.

The compositions of the present disclosure may have a concentration of the dendrimer of about 1.0 mM or less. The composition may have a concentration of about 1.0 mM or less, about 0.9 mM or less, about 0.8 mM or less, about 0.7 mM or less, about 0.6 mM or less, about 0.5 mM or less, about 0.4 mM or less, about 0.3 mM or less, about 0.2 mM or less, or about 0.1 mM or less of the dendrimer. The composition may have a concentration of about 0.05 mM or greater, about 0.1 mM or greater, about 0.2 mM or greater, about 0.3 mM or greater, about 0.4 mM or greater, about 0.5 mM or greater, about 0.6 mM or greater, about 0.7 mM or greater, about 0.8 mM or greater, or about 0.9 mM or greater of the dendrimer.

Examples of dendrimers include, but are not necessarily limited to, poly(amidoamine) (PAMAM), poly(propyleneimine) (PPI), poly(lysine), poly(glycerol) or a hyperbranched structure. The hyperbranched structure may be a dendrigraft, a polyester, a polyamide, or a polyalcohol.

The core of PAMAM is a diamine. PAMAM is synthesized by reacting the diamine with methyl acrylate, and then another diamine to make the generation-0 (G-0) PAMAM. Successive reactions create higher generations, which tend to have different properties. Lower generations can be thought of as flexible molecules with no appreciable inner regions, while medium sized (G-3 or G-4) do have internal space that is essentially separated from the outer shell of the dendrimer. Very large (G-7 and greater) dendrimers can be thought of more like solid particles with very dense surfaces due to the structure of their outer shell.

The surface groups of the dendrimer of the composition may be amine, hydroxyl, carboxylate, pyrrolidinone, cysteamine, or PEG moieties.

The core of the dendrimer of the composition may be ethylenediamine, diaminobutane, 1,12-diaminododecane, or cysteamine.

In an embodiment, the dendrimer may be a generation 4 PAMAM dendrimer comprising a diaminobutane core and amine surface groups. This dendrimer may also be referred to herein as a PAMAM G4-amine dendrimer.

C. Resveratrol

The compositions include resveratrol associated with dendrimer in the dendrimer-resveratrol complex.

At least about 75%, at least about 80%, at least about 85%, at least about 90%, at least about 95%, at least about 96%, at least about 97%, at least about 98%, at least about 99%, by weight, of the resveratrol in the composition may be associated with the dendrimer. The composition may be essentially free of free resveratrol (i.e., the composition may be essentially free of non-complexed resveratrol) The composition may have essentially no free resveratrol. The composition may have no free resveratrol.

The concentration of resveratrol associated with the dendrimer may be at least about 0.003 mM, as measured according to the total volume of the composition at pH 7. The concentration of resveratrol associated with the dendrimer may be at least about 0.001 mM, at least about 0.002 mM, at least about 0.003 mM, at least about 0.004 mM, at least about 0.005 mM, at least about 0.006 mM, at least about 0.007 mM, at least about 0.008 mM, at least about 0.009 mM, at least about 0.01 mM, at least about 0.011 mM, at least about 0.012 mM, at least about 0.013 mM, at least about 0.014 mM, at least about 0.015 mM, at least about 0.016 mM, at least about 0.017 mM, at least about 0.018 mM, at least about 0.019 mM, at least about 0.02 mM, at least about 0.021 mM, at least about 0.022 mM, at least about 0.023 mM, at least about 0.024 mM, at least about 0.025 mM, at least about 0.026 mM, at least about 0.027 mM, at least about 0.028 mM, at least about 0.029 mM, at least about 0.03 mM, at least about 0.031 mM, at least about 0.032 mM, at least about 0.033 mM, at least about 0.034 mM, at least about 0.035 mM, at least about 0.036 mM, at least about 0.037 mM, at least about 0.038 mM, at least about 0.039 mM, at least about 0.03 mM, at least about 0.04 mM, at least about 0.05 mM, at least about 0.06 mM, at least about 0.07 mM, at least about 0.08 mM, at least about 0.09 mM, or at least about 0.1 mM, as measured according to the total volume of the composition at pH 7. The concentration of the resveratrol associated with the dendrimer may improve an aqueous solubility over neat resveratrol.

The concentration of resveratrol associated with the dendrimer may be at least about 0.001 mM, at least about 0.002 mM, at least about 0.003 mM, at least about 0.004 mM, at least about 0.005 mM, at least about 0.006 mM, at least about 0.007 mM, at least about 0.008 mM, at least about 0.009 mM, at least about 0.01 mM, at least about 0.011 mM, at least about 0.012 mM, at least about 0.013 mM, at least about 0.014 mM, at least about 0.015 mM, at least about 0.016 mM, at least about 0.017 mM, at least about 0.018 mM, at least about 0.019 mM, or at least about 0.02 mM, as measured according to the total volume of the composition at pH 2.5. The concentration of the resveratrol associated with the dendrimer may improve aqueous solubility over neat resveratrol.

The composition may include dendrimer-resveratrol complex in an amount, by weight, of at least about 1%, at least about 2%, at least about 3%, at least about 4%, at least about 5%, at least about 6%, at least about 7%, at least about 8%, at least about 9%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99%. The composition may comprise dendrimer-resveratrol complex in an amount, by weight, of less than about 1%, less than about 2%, less than about 3%, less than about 4%, less than about 5%, less than about 6%, less than about 7%, less than about 8%, less than about 9%, less than about 10%, less than about 15%, less than about 20%, less than about 25%, less than about 30%, less than about 35%, less than about 40%, less than about 45%, less than about 50%, less than about 55%, less than about 60%, less than about 65%, less than about 70%, less than about 75%, less than about 80%, less than about 85%, less than about 90%, less than about 91%, less than about 92%, less than about 93%, less than about 94%, less than about 95%, less than about 96%, less than about 97%, less than about 98%, or less than about 99%. The composition may comprise dendrimer-resveratrol complex in an amount, by weight, of about 1% to about 50%, about 1% to about 45%, about 1% to about 40%, about 1% to about 35%, about 1% to about 30%, about 1% to about 25%, about 1% to about 20%, about 1% to about 15%, about 1% to about 10%, about 1% to about 9%, about 1% to about 8%, about 1% to about 7%, about 1% to about 6%, about 1% to about 5%, about 1% to about 4%, about 1% to about 3%, about 1% to about 2%, about 1% to about 99%, about 5% to about 95%, about 10% to about 90%, about 20% to about 80%, about 30% to about 70%, about 40% to about 60%, about 40% to about 50%, about 50% to about 60%, about 50% to about 99%, about 55% to about 99%, about 60% to about 99%, about 65% to about 99%, about 70% to about 99%, about 75% to about 99%, about 80% to about 99%, about 85% to about 99%, about 90% to about 99%, about 91% to about 99%, about 92% to about 99%, about 93% to about 99%, about 94% to about 99%, about 95% to about 99%, about 96% to about 99%, about 97% to about 99%, or about 98% to about 99%.

D. Other Components of the Composition

1) Solvents

The composition may further comprise a solvent. Suitable solvents will be capable of having dendrimer-resveratrol complex dispersed or dissolved therein. Examples of solvents include, but are not limited to, water and other non-organic solvents, such as liquid ammonia and sulfur dioxide. The composition may comprise solvent in an amount, by weight, at least about 1%, at least about 2%, at least about 3%, at least about 4%, at least about 5%, at least about 6%, at least about 7%, at least about 8%, at least about 9%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99%. The composition may comprise solvent in an amount, by weight, of less than about 1%, less than about 2%, less than about 3%, less than about 4%, less than about 5%, less than about 6%, less than about 7%, less than about 8%, less than about 9%, less than about 10%, less than about 15%, less than about 20%, less than about 25%, less than about 30%, less than about 35%, less than about 40%, less than about 45%, less than about 50%, less than about 55%, less than about 60%, less than about 65%, less than about 70%, less than about 75%, less than about 80%, less than about 85%, less than about 90%, less than about 91%, less than about 92%, less than about 93%, less than about 94%, less than about 95%, less than about 96%, less than about 97%, less than about 98%, or less than about 99%. The composition may comprise solvent in an amount, by weight, of about 1% to about 50%, about 1% to about 45%, about 1% to about 40%, about 1% to about 35%, about 1% to about 30%, about 1% to about 25%, about 1% to about 20%, about 1% to about 15%, about 1% to about 10%, about 1% to about 9%, about 1% to about 8%, about 1% to about 7%, about 1% to about 6%, about 1% to about 5%, about 1% to about 4%, about 1% to about 3%, about 1% to about 2%, about 1% to about 99%, about 5% to about 95%, about 10% to about 90%, about 20% to about 80%, about 30% to about 70%, about 40% to about 60%, about 40% to about 50%, about 50% to about 60%, about 50% to about 99%, about 55% to about 99%, about 60% to about 99%, about 65% to about 99%, about 70% to about 99%, about 75% to about 99%, about 80% to about 99%, about 85% to about 99%, about 90% to about 99%, about 91% to about 99%, about 92% to about 99%, about 93% to about 99%, about 94% to about 99%, about 95% to about 99%, about 96% to about 99%, about 97% to about 99%, or about 98% to about 99%. The balance of the composition may be water or non-organic solvent. The composition may be essentially free of organic solvent. The composition may be essentially free of solvent.

2) Antioxidants

Compositions of the present disclosure may include at least one antioxidant. The inclusion of an antioxidant may improve the therapeutic benefits of the composition, and may protect resveratrol from oxidative damage.

Exemplary antioxidants include, but are not limited to, ascorbic acid (vitamin C) and salts and esters thereof (e.g., sodium ascorbate, ascorbyl phosphate and salts thereof such as magnesium ascorbyl phosphate, ascorbyl esters of fatty acids such as ascorbyl palmitate), epichlorocatechin, circumin, tocopherol (vitamin E) and salts and esters thereof (e.g., tocopheryl acetate, tocopheryl phosphate), butylated hydroxy benzoic acids and their salts, butylated hydroxytoluene, butylated hydroxyanisole, 6-hydroxy-2,5,7,8-tetramethylchroman-2-carboxylic acid (commercially available under the trade name Trolox™), gallic acid and its alkyl esters (e.g., propyl gallate), uric acid and its salts and alkyl esters, sorbic acid and its salts, amines (e.g., N,N-diethylhydroxylamine, amino-guanidine), sulfhydryl compounds (e.g., glutathione), sodium metabisulfite, and dihydroxy fumaric acid and its salts may be used.

An antioxidant or a mixture of antioxidants may be included in the composition at an amount, by weight, of up to about 0.01%, up to about 0.02%, up to about 0.03%, up to about 0.04%, up to about 0.05%, up to about 0.06%, up to about 0.07%, up to about 0.08%, up to about 0.09%, up to about 0.10%, up to about 0.11%, up to about 0.12%, up to about 0.13%, up to about 0.14%, up to about 0.15%, up to about 0.16%, up to about 0.17%, up to about 0.18%, up to about 0.19%, up to about 0.20%, up to about 0.25%, up to about 0.30%, up to about 0.35%, up to about 0.40%, up to about 0.45%, up to about 0.50%, up to about 0.55%, up to about 0.60%, at least about 0.01%, at least about 0.02%, at least about 0.03%, at least about 0.04%, at least about 0.05%, at least about 0.06%, at least about 0.07%, at least about 0.08%, at least about 0.09%, at least about 0.10%, at least about 0.11%, at least about 0.12%, at least about 0.13%, at least about 0.14%, at least about 0.15%, at least about 0.16%, at least about 0.17%, at least about 0.18%, at least about 0.19%, at least about 0.20%, at least about 0.25%, at least about 0.30%, at least about 0.35%, at least about 0.40%, at least about 0.45%, at least about 0.50%, at least about 0.55%, at least about 0.60%, about 0.01%, about 0.02%, about 0.03%, about 0.04%, about 0.05%, about 0.06%, about 0.07%, about 0.08%, about 0.09%, about 0.10%, about 0.11%, about 0.12%, about 0.13%, about 0.14%, about 0.15%, about 0.16%, about 0.17%, about 0.18%, about 0.19%, about 0.20%, about 0.25%, about 0.30%, about 0.35%, about 0.40%, about 0.45%, about 0.50%, about 0.55%, or about 0.60%.

3) Other Components or Additives

Compositions of the present disclosure may include at least one of the following, or any combination thereof: a glycol; a chelating agent; an emollient (such as coconut oil, cetyl esters, and certain silicones); a humectant (such as glycerin); an occlusive agent (such as petrolatum, mineral oil, and dimethicone); other moisturizers to provide moisturizing, skin softening, skin barrier maintenance, anti-irritation, or other skin health benefits; an emulsifier (such as glyceryl stearate and stearic acid), a preservative, which may have anti-microbial activity; a steroidal anti-inflammatory agent; a nonsteroidal anti-inflammatory agent; a retinoid; an opacifier (such as titanium dioxide); a penetration enhancer; a vitamin; a fragrance; a colorant; an exfoliant; an anti-acne agent; an anti-aging agent; a body lotion; a body treatment; a toner; a facial moisturizer; a facial treatment; makeup foundation; or any skin care product. These components may be added in an amount that is requisite with obtaining the desired effect in the composition. In some embodiments, the compositions of the present disclosure include a retinoid, such as retinol.

A glycol or a mixture of glycols may be included in the composition at an amount, by weight, of at least about 0.1%, at least about 0.2%, at least about 0.3%, at least about 0.4%, at least about 0.5%, at least about 0.6%, at least about 0.7%, at least about 0.8%, at least about 0.9%, at least about 1.0%, at least about 1.5%, at least about 2.0%, at least about 2.5%, at least about 3.0%, at least about 3.5%, at least about 4.0%, at least about 4.5%, at least about 5.0%, at least about 5.5%, at least about 6.0%, at least about 6.5%, at least about 7.0%, at least about 7.5%, at least about 8.0%, at least about 8.5%, at least about 9.0%, at least about 9.5%, at least about 10%, up to about 0.1%, up to about 0.2%, up to about 0.3%, up to about 0.4%, up to about 0.5%, up to about 0.6%, up to about 0.7%, up to about 0.8%, up to about 0.9%, up to about 1.0%, up to about 1.5%, up to about 2.0%, up to about 2.5%, up to about 3.0%, up to about 3.5%, up to about 4.0%, up to about 4.5%, up to about 5.0%, up to about 5.5%, up to about 6.0%, up to about 6.5%, up to about 7.0%, up to about 7.5%, up to about 8.0%, up to about 8.5%, up to about 9.0%, up to about 9.5%, up to about 10%, about 0.1%, about 0.2%, about 0.3%, about 0.4%, about 0.5%, about 0.6%, about 0.7%, about 0.8%, about 0.9%, about 1.0%, about 1.5%, about 2.0%, about 2.5%, about 3.0%, about 3.5%, about 4.0%, about 4.5%, about 5.0%, about 5.5%, about 6.0%, about 6.5%, about 7.0%, about 7.5%, about 8.0%, about 8.5%, about 9.0%, about 9.5%, or about 10%.

A chelating agent or a mixture of chelating agents may be included in the composition at an amount, by weight, of up to about 0.01%, up to about 0.02%, up to about 0.03%, up to about 0.04%, up to about 0.05%, up to about 0.06%, up to about 0.07%, up to about 0.08%, up to about 0.09%, up to about 0.10%, up to about 0.15%, up to about 0.20%, up to about 0.25%, up to about 0.30%, up to about 0.35%, up to about 0.40%, up to about 0.45%, up to about 0.50%, up to about 0.55%, up to about 0.60%, up to about 0.70%, up to about 0.80%, up to about 0.90%, up to about 1.0%, at least about 0.01%, at least about 0.02%, at least about 0.03%, at least about 0.04%, at least about 0.05%, at least about 0.06%, at least about 0.07%, at least about 0.08%, at least about 0.09%, at least about 0.10%, at least about 0.15%, at least about 0.20%, at least about 0.25%, at least about 0.30%, at least about 0.35%, at least about 0.40%, at least about 0.45%, at least about 0.50%, at least about 0.55%, at least about 0.60%, at least about 0.70%, at least about 0.80%, at least about 0.90%, at least about 1.0%, about 0.01%, about 0.02%, about 0.03%, about 0.04%, about 0.05%, about 0.06%, about 0.07%, about 0.08%, about 0.09%, about 0.10%, about 0.15%, about 0.20%, about 0.25%, about 0.30%, about 0.35%, about 0.40%, about 0.45%, about 0.50%, about 0.55%, about 0.60%, about 0.70%, about 0.80%, about 0.90%, or about 1.0%.

An emulsifier or mixture of emulsifiers may be included in the composition at an amount, by weight, of at least about 0.1%, at least about 0.2%, at least about 0.3%, at least about 0.4%, at least about 0.5%, at least about 0.6%, at least about 0.7%, at least about 0.8%, at least about 0.9%, at least about 1.0%, at least about 1.5%, at least about 2.0%, at least about 2.5%, at least about 3.0%, at least about 3.5%, at least about 4.0%, at least about 4.5%, at least about 5.0%, at least about 5.5%, at least about 6.0%, at least about 6.5%, at least about 7.0%, at least about 7.5%, at least about 8.0%, at least about 8.5%, at least about 9.0%, at least about 9.5%, at least about 10%, up to about 0.1%, up to about 0.2%, up to about 0.3%, up to about 0.4%, up to about 0.5%, up to about 0.6%, up to about 0.7%, up to about 0.8%, up to about 0.9%, up to about 1.0%, up to about 1.5%, up to about 2.0%, up to about 2.5%, up to about 3.0%, up to about 3.5%, up to about 4.0%, up to about 4.5%, up to about 5.0%, up to about 5.5%, up to about 6.0%, up to about 6.5%, up to about 7.0%, up to about 7.5%, up to about 8.0%, up to about 8.5%, up to about 9.0%, up to about 9.5%, up to about 10%, about 0.1%, about 0.2%, about 0.3%, about 0.4%, about 0.5%, about 0.6%, about 0.7%, about 0.8%, about 0.9%, about 1.0%, about 1.5%, about 2.0%, about 2.5%, about 3.0%, about 3.5%, about 4.0%, about 4.5%, about 5.0%, about 5.5%, about 6.0%, about 6.5%, about 7.0%, about 7.5%, about 8.0%, about 8.5%, about 9.0%, about 9.5%, or about 10%.

A conditioning agent or mixture of conditioning agents may be included in the composition at an amount, by weight, of at least about 0.5%, at least about 0.75%, at least about 1.0%, at least about 1.5%, at least about 2.0%, at least about 2.5%, at least about 3.0%, at least about 3.5%, at least about 4.0%, at least about 4.5%, at least about 5.0%, up to about 0.5%, up to about 0.75%, up to about 1.0%, up to about 1.5%, up to about 2.0%, up to about 2.5%, up to about 3.0%, up to about 3.5%, up to about 4.0%, up to about 4.5%, up to about 5.0%, about 0.5%, about 0.75%, about 1.0%, about 1.5%, about 2.0%, about 2.5%, about 3.0%, about 3.5%, about 4.0%, about 4.5%, or about 5.0%.

A preservative or mixture of preservatives may be included in the composition at an amount, by weight, of up to about 0.01%, up to about 0.02%, up to about 0.03%, up to about 0.04%, up to about 0.05%, up to about 0.06%, up to about 0.07%, up to about 0.08%, up to about 0.09%, up to about 0.10%, up to about 0.15%, up to about 0.20%, up to about 0.25%, up to about 0.30%, up to about 0.35%, up to about 0.40%, up to about 0.45%, up to about 0.50%, up to about 0.55%, up to about 0.60%, up to about 0.65%, up to about 0.70%, up to about 0.75%, up to about 0.80%, up to about 0.85%, up to about 0.90%, up to about 0.95%, up to about 1.0%, at least about 0.01%, at least about 0.02%, at least about 0.03%, at least about 0.04%, at least about 0.05%, at least about 0.06%, at least about 0.07%, at least about 0.08%, at least about 0.09%, at least about 0.10%, at least about 0.15%, at least about 0.20%, at least about 0.25%, at least about 0.30%, at least about 0.35%, at least about 0.40%, at least about 0.45%, at least about 0.50%, at least about 0.55%, at least about 0.60%, at least about 0.65%, at least about 0.70%, at least about 0.75%, at least about 0.80%, at least about 0.85%, at least about 0.90%, at least about 0.95%, at least about 1.0%, about 0.01%, about 0.02%, about 0.03%, about 0.04%, about 0.05%, about 0.06%, about 0.07%, about 0.08%, about 0.09%, about 0.10%, about 0.15%, about 0.20%, about 0.25%, about 0.30%, about 0.35%, about 0.40%, about 0.45%, about 0.50%, about 0.55%, about 0.60%, about 0.65%, about 0.70%, about 0.75%, about 0.80%, about 0.85%, about 0.90%, about 0.95%, or about 1.0%.

D. Properties of the Composition 1) pH

The pH of compositions including the dendrimer-resveratrol complex can affect one or more of solubility, stability, and efficacy of the composition. For example, lower pH may result in lower solubility of the resveratrol associated with the dendrimer complex. The pH of the composition may be about 7. The pH of the composition may be about 2 to about 10, about 2 to about 9, about 2 to about 8, about 2 to about 7, about 2 to about 6, about 2 to about 5, about 2 to about 4, about 2 to about 3, about 3 to about 10, about 3 to about 9, about 3 to about 8, about 3 to about 7, about 3 to about 6, about 3 to about 5, about 3 to about 4, about 4 to about 10, about 4 to about 9, about 4 to about 8, about 4 to about 7, about 4 to about 6, about 4 to about 5, about 5 to about 10, about 5 to about 9, about 5 to about 8, about 5 to about 7, about 5 to about 6, about 6 to about 10, about 6 to about 9, about 6 to about 8, about 6 to about 7, about 7 to about 10, about 7 to about 9, or about 7 to about 8. The pH of the composition may be about 2, about 3, about 4, about 5, about 6, about 7, about 8, about 9, or about 10. The pH of the composition may be about 10 or less, about 9 or less, about 8 or less, about 7 or less, about 6 or less, about 5 or less, about 4 or less, or about 3 or less. The pH of the composition may be 2, 2.5, 3, 3.5, 4, 4.5, 5, 5.5, 6, 6.5, 7, 7.5, 8, 8.5, 9, 9.5, or 10.

Composition pH can be adjusted with acid or base, if necessary. Any acid or base compatible with the components of the composition can be used. Exemplary acids include citric acid, gluconic acid, lactic acid, acetic acid, and glycolic acid. Exemplary bases include sodium hydroxide, potassium hydroxide, and triethanolamine.

2) Solubility

The solubility of resveratrol associated with dendrimer in a complex such as the composition of the present disclosure can be enhanced over neat resveratrol. The concentration of resveratrol associated with dendrimer can be determined via laboratory analytical methods such as HPLC. Formulations containing the composition can be manufactured and then tested by these methods. Specifically, the solubility of resveratrol in a composition comprising a resveratrol-PAMAM G4-amine dendrimer complex at pH 7 can be determined.

The aqueous solubility of the resveratrol associated with the dendrimer may be at least about 10 times greater, at least about 20 times greater, at least about 30 times greater, at least about 40 times greater, at least about 50 times greater, at least about 60 times greater, at least about 70 times greater, at least about 80 times greater, at least about 90 times greater, at least about 100 times greater, at least about 110 times greater, at least about 120 times greater, at least about 130 times greater, at least about 140 times greater, at least about 150 times greater, at least about 160 times greater, at least about 170 times greater, at least about 180 times greater, at least about 190 times greater, at least about 200 times greater, at least about 210 times greater, at least about 220 times greater, at least about 230 times greater, at least about 240 times greater, at least about 250 times greater, at least about 260 times greater, at least about 270 times greater, at least about 280 times greater, at least about 290 times greater, or at least about 300 times greater than the aqueous solubility of neat resveratrol, as measured at pH 7.

The aqueous solubility of the resveratrol associated with the dendrimer may be at least about 10 times greater, at least about 20 times greater, at least about 30 times greater, at least about 40 times greater, at least about 50 times greater, at least about 60 times greater, at least about 70 times greater, at least about 80 times greater, at least about 90 times greater, or at least about 100 times greater than the aqueous solubility of neat resveratrol, as measured at pH 2, at pH 2.5, at pH 3, at pH 3.5, at pH 4, at pH 4.5, at pH 5, at pH 5.5, at pH 6, at pH 6.5, at pH 7, at pH 7.5, at pH 8, at pH 8.5, at pH 9, at pH 9.5, or at pH 10. Dissolution rates of the composition in solid form can also be measured. For example, the dissolution of the composition can be measured in simulated gastric and intestinal fluids. The time to dissolution of the composition in simulated gastric fluid may be less than about 1 hour, less than about 55 minutes, less than about 50 minutes, less than about 45 minutes, less than about 40 minutes, less than about 35 minutes, less than about 30 minutes, less than about 25 minutes, less than about 20 minutes, less than about 15 minutes, less than about 10 minutes, or less than about 5 minutes. The time to dissolution of the composition in simulated intestinal fluid may be less than about 1 hour, less than about 55 minutes, less than about 50 minutes, less than about 45 minutes, less than 40 minutes, less than about 35 minutes, less than about 30 minutes, less than about 25 minutes, less than about 20 minutes, less than about 15 minutes, less than about 10 minutes, or less than about 5 minutes.

3) Stability

Associating resveratrol with a dendrimer in a complex may enhance stability over neat resveratrol. The concentration of non-degraded resveratrol over time associated with dendrimer can be determined via laboratory analytical methods such as HPLC. After determining the initial amount (or concentration) of resveratrol in a manufactured composition, samples containing the manufactured composition can be kept at predetermined temperatures for predetermined amounts of time. The sample can then be analyzed via HPLC to determine the amount of resveratrol in the composition. This amount of resveratrol can be compared to the initially determined amount. This comparison amount can be used to determine the percent degradation. For example, a sample of a composition may initially contain 1.0 mg/mL resveratrol, and after 4 days, the same sample may contain 0.95 mg/mL resveratrol. In this hypothetical example, the resveratrol has degraded by 5%. Specifically, the stability of resveratrol in a composition comprising a resveratrol-PAMAM G4-amine dendrimer complex at pH 7 can be determined at ambient (room), elevated, and reduced temperatures.

The resveratrol associated with the dendrimer may degrade less than about 30%, less than about 29%, less than about 28%, less than about 27%, less than about 26%, less than about 25%, less than about 24%, less than about 23%, less than about 22%, less than about 21%, less than about 20%, less than about 19%, less than about 18%, less than about 17%, less than about 16%, less than about 15%, less than about 14%, less than about 13%, less than about 12%, less than about 11%, less than about 10%, less than about 9%, less than about 8%, less than about 7%, less than about 6%, or less than about 5% after 4 days at ambient temperature.

The resveratrol associated with the dendrimer may degrade less than about 85%, less than about 84%, less than about 83%, less than about 82%, less than about 81%, less than about 80%, less than about 79%, less than about 78%, less than about 77%, less than about 76%, less than about 75%, less than about 74%, less than about 73%, less than about 72%, less than about 71%, less than about 70%, less than about 69%, less than about 68%, less than about 67%, less than about 66%, less than about 65%, less than about 64%, less than about 63%, less than about 62%, less than about 61%, or less than about 60% after 11 days at ambient temperature.

Anti-oxidant efficacy of the composition can also be measured by use of a DPPH (1,1-diphenyl-2-picrylhydrazyl) assay. In this assay, changes in color of the composition can be measured at certain wavelengths of light using a UV/visible light spectrophotometer. When a DPPH free radical reacts with an antioxidant compound, it is reduced. DPPH is a well-known radical and a trap ("scavenger") for other radicals. Therefore, rate reduction of a chemical reaction upon addition of DPPH is used as an indicator of the radical nature of that reaction. Because of a strong absorption band centered at about 520 nm, the DPPH radical has a deep violet color in solution, and it becomes colorless or pale yellow when neutralized. In particular, the anti-oxidant efficacy of a resveratrol-PAMAM G4-amine dendrimer complex at pH 7 can be determined at predetermined timepoints.

The composition may demonstrate greater than about 40% inhibition, greater than about 45% inhibition, greater than about 50% inhibition, greater than about 55% inhibition, greater than about 60% inhibition, or greater than about 64% inhibition, of the DPPH oxidation at 15 minutes. The composition may demonstrate greater than 30% inhibition, greater than about 35% inhibition, greater than about 40% inhibition, greater than about 45% inhibition, greater than about 50% inhibition, or greater than about 51% inhibition, of the DPPH oxidation at 19 hours.

4) Transdermal Permeation

Compositions comprising the dendrimer-resveratrol complexes of the present disclosure may improve transdermal permeation of resveratrol when the compositions are applied topically to skin, compared to compositions having uncomplexed neat resveratrol. The concentration of resveratrol associated with dendrimer that permeates through skin over a period of time can be determined by use of Franz Diffusion Cells (FDC) and rat skin samples. Formulations containing the composition can be manufactured and then tested by these methods. Specifically, the transdermal permeation of resveratrol in a composition comprising a resveratrol-PAMAM G4-amine dendrimer complex at pH 7 can be determined.

At least about 50%, by weight, of the resveratrol associated with dendrimer may permeate the skin in 20 minutes or less in a transdermal permeation study utilizing Franz Diffusion Cells and rat skin samples. At least about 30%, at least about 35%, at least about 40%, at least about 45%, at least about 50%, at least about 55%, at least about 60%, at least about 65%, at least about 70%, at least about 75%, or at least about 78% by weight, of the resveratrol associated with dendrimer may permeate the skin within a period of time in a transdermal permeation study utilizing Franz Diffusion Cells and rat skin samples. The period of time may be 10 minutes or less, 15 minutes or less, 20 minutes or less, 25 minutes or less, 30 minutes or less, 35 minutes or less, 40 minutes or less, 45 minutes or less, 50 minutes or less, 55 minutes or less, or 60 minutes or less.

Less than 60%, by weight, of the resveratrol associated with dendrimer may be found as a deposit on the skin after 20 minutes in a transdermal permeation study utilizing Franz Diffusion Cells and rat skin samples. Less than about 22%, less than about 25%, less than about 30%, less than about 35%, less than about 40%, less than about 45%, less than about 50%, less than about 55%, less than about 65%, less than about 70%, or less than about 75% by weight, of the resveratrol associated with dendrimer may be found as a deposit on the skin after a period of time in a transdermal permeation study utilizing Franz Diffusion Cells and rat skin samples. The period of time may be 10 minutes, 15 minutes, 20 minutes, 25 minute, 30 minutes, 35 minutes, 40 minutes, 45 minutes, 50 minutes, 55 minutes or 60 minutes.

E. Embodiments of the Composition

In an embodiment, the composition may comprise a dendrimer-resveratrol complex, the composition being essentially free of organic solvent; wherein the composition comprises water; wherein the pH of the composition is about 7.

In an embodiment, the composition may comprise a dendrimer-resveratrol complex, the composition being essentially free of organic solvent; wherein the composition comprises water; wherein the pH of the composition is about 7; wherein at least 95%, by weight, of the resveratrol in the composition is associated with the dendrimer.

In an embodiment, the composition may comprise a dendrimer-resveratrol complex, the composition being essentially free of organic solvent; wherein the composition comprises water; wherein the pH of the composition is about 7; wherein at least 95%, by weight, of the resveratrol in the composition is associated with the dendrimer; wherein the aqueous solubility of the resveratrol associated with the dendrimer is at least 40 times greater than the aqueous solubility of neat resveratrol; wherein the concentration of resveratrol associated with the dendrimer is at least 0.003 mM, as measured according to the total volume of the composition.

In an embodiment, the composition may comprise a dendrimer-resveratrol complex, the composition being essentially free of organic solvent; wherein the composition comprises water; wherein the pH of the composition is about 7; wherein at least 95%, by weight, of the resveratrol in the composition is associated with the dendrimer; wherein the aqueous solubility of the resveratrol associated with the dendrimer is at least 100 times greater than the aqueous solubility of neat resveratrol; wherein the concentration of resveratrol associated with the dendrimer is at least 0.01 mM, as measured according to the total volume of the composition.

In an embodiment, the composition may comprise a dendrimer-resveratrol complex, the composition being essentially free of organic solvent; wherein the composition comprises water; wherein the pH of the composition is about 7; wherein at least 95%, by weight, of the resveratrol in the composition is associated with the dendrimer; wherein the aqueous solubility of the resveratrol associated with the dendrimer is at least 40 times greater than the aqueous solubility of neat resveratrol; wherein the concentration of resveratrol associated with the dendrimer is at least 0.003 mM, as measured according to the total volume of the composition; wherein the resveratrol associated with the dendrimer degrades less than 10% after 4 days at ambient temperature.

In an embodiment, the composition may comprise a dendrimer-resveratrol complex, the composition being essentially free of organic solvent; wherein the composition comprises water; wherein the pH of the composition is about 7; wherein at least 95%, by weight, of the resveratrol in the composition is associated with the dendrimer; wherein the aqueous solubility of the resveratrol associated with the dendrimer is at least 100 times greater than the aqueous solubility of neat resveratrol; wherein the concentration of resveratrol associated with the dendrimer is at least 0.01 mM, as measured according to the total volume of the composition; wherein the resveratrol associated with the dendrimer degrades less than 10% after 4 days at ambient temperature.

In an embodiment, the composition may comprise a dendrimer-resveratrol complex, the composition being essentially free of organic solvent; wherein the composition comprises water; wherein the pH of the composition is about 7; wherein at least 95%, by weight, of the resveratrol in the composition is associated with the dendrimer; wherein the aqueous solubility of the resveratrol associated with the dendrimer is at least 40 times greater than the aqueous solubility of neat resveratrol; wherein the concentration of resveratrol associated with the dendrimer is at least 0.003 mM, as measured according to the total volume of the composition; wherein the resveratrol associated with the dendrimer degrades less than 10% after 4 days at ambient temperature; wherein at least 50%, by weight, of the resveratrol associated with dendrimer permeates skin in 20 minutes or less in a transdermal permeation study utilizing Franz Diffusion Cells and rat skin samples.

In an embodiment, the composition may comprise a dendrimer-resveratrol complex, the composition being essentially free of organic solvent; wherein the composition comprises water; wherein the pH of the composition is about 7; wherein at least 95%, by weight, of the resveratrol in the composition is associated with the dendrimer; wherein the aqueous solubility of the resveratrol associated with the dendrimer is at least 100 times greater than the aqueous solubility of neat resveratrol; wherein the concentration of resveratrol associated with the dendrimer is at least 0.01 mM, as measured according to the total volume of the composition; wherein the resveratrol associated with the dendrimer degrades less than 10% after 4 days at ambient temperature; wherein at least 50%, by weight, of the resveratrol associated with dendrimer permeates skin in 20 minutes or less in a transdermal permeation study utilizing Franz Diffusion Cells and rat skin samples.

In an embodiment, the composition may comprise a dendrimer-resveratrol complex, the composition being essentially free of organic solvent; wherein the composition comprises water; wherein the pH of the composition is about 7; wherein at least 95%, by weight, of the resveratrol in the composition is associated with the dendrimer; wherein the aqueous solubility of the resveratrol associated with the dendrimer is at least 40 times greater than the aqueous solubility of neat resveratrol; wherein the resveratrol associated with the dendrimer degrades less than 10% after 4 days at ambient temperature; wherein at least 50%, by weight, of the resveratrol associated with dendrimer permeates skin in 20 minutes or less in a transdermal permeation study utilizing Franz Diffusion Cells and rat skin samples; the composition comprising about 1.0 mM dendrimer or less.

In an embodiment, the composition may comprise a dendrimer-resveratrol complex, the composition being essentially free of organic solvent; wherein the composition comprises water; wherein the pH of the composition is about 7; wherein at least 95%, by weight, of the resveratrol in the composition is associated with the dendrimer; wherein the aqueous solubility of the resveratrol associated with the dendrimer is at least 40 times greater than the aqueous solubility of neat resveratrol; wherein the resveratrol associated with the dendrimer degrades less than 10% after 4 days at ambient temperature; wherein at least 50%, by weight, of the resveratrol associated with dendrimer permeates skin in 20 minutes or less in a transdermal permeation study utilizing Franz Diffusion Cells and rat skin samples; the composition comprising about 0.40 mM dendrimer or less.

In an embodiment, the composition may comprise a dendrimer-resveratrol complex, the composition being essentially free of organic solvent; wherein the composition comprises water; wherein the pH of the composition is about 7; wherein at least 95%, by weight, of the resveratrol in the composition is associated with the dendrimer; wherein the aqueous solubility of the resveratrol associated with the dendrimer is at least 40 times greater than the aqueous solubility of neat resveratrol; wherein the resveratrol associated with the dendrimer degrades less than 10% after 4 days at ambient temperature; wherein at least 50%, by weight, of the resveratrol associated with dendrimer permeates skin in 20 minutes or less in a transdermal permeation study utilizing Franz Diffusion Cells and rat skin samples; the composition comprising about 1.0 mM dendrimer or less; wherein the dendrimer is PAMAM G4-amine dendrimer.

In an embodiment, the composition may comprise a dendrimer-resveratrol complex, the composition being essentially free of organic solvent; wherein the composition comprises water; wherein the pH of the composition is about 7; wherein at least 95%, by weight, of the resveratrol in the composition is associated with the dendrimer; wherein the aqueous solubility of the resveratrol associated with the dendrimer is at least 40 times greater than the aqueous solubility of neat resveratrol; wherein the resveratrol associated with the dendrimer degrades less than 10% after 4 days at ambient temperature; wherein at least 50%, by weight, of the resveratrol associated with dendrimer permeates skin in 20 minutes or less in a transdermal permeation study utilizing Franz Diffusion Cells and rat skin samples; the composition comprising about 0.40 mM dendrimer or less; wherein the dendrimer is PAMAM G4-amine dendrimer.

Compositions may include but are not limited to the following:
 (1) a composition comprising about 0.70 mM dendrimer and about 0.004 mM resveratrol;
 (2) a composition comprising about 0.70 mM dendrimer and about 0.011 mM resveratrol;
 (3) a composition comprising about 0.07 mM dendrimer and about 0.004 mM resveratrol;
 (4) a composition comprising about 0.07 mM dendrimer and about 0.005 mM resveratrol;
 (5) a composition comprising about 0.70 mM PAMAM G4-amine dendrimer and about 0.004 mM resveratrol;
 (6) a composition comprising about 0.70 mM PAMAM G4-amine dendrimer and about 0.011 mM resveratrol;
 (7) a composition comprising about 0.07 mM PAMAM G4-amine dendrimer and about 0.004 mM resveratrol; and (8) a composition comprising about 0.07 mM PAMAM G4-amine dendrimer and about 0.005 mM resveratrol.

3. Methods for Preparing the Compositions

The disclosure also provides a method of making the compositions. The method may comprise mixing resveratrol, dendrimer, and solvent to form a mixture comprising a dendrimer-resveratrol complex; and filtering the mixture to form the composition. Suitable equipment for mixing the components include, but are not limited to, magnetic stir bars in conjunction with magnetic stir plates, stirring rods, overhead stirrers, centrifuges, sonicators and shakers. Use of this equipment may promote the dissolving of resveratrol in the solvent. The components of the composition may be mixed for up to about 5 minutes, about 10 minutes, about 15 minutes, about 20 minutes, about 30 minutes, about 40 minutes, about 50 minutes, about 1 hour, about 2 hours, about 3 hours, about 4 hours, about 5 hours, about 6 hours, about 7 hours, about 8 hours, about 9 hours, about 10 hours, about 11 hours, about 12 hours, about 14 hours, about 16 hours, about 18 hours, or about 24 hours.

Filtration of the final composition may remove excess solids such as free resveratrol not associated with the dendrimer-resveratrol complex. Suitable equipment for filtering the composition include, but are not limited to, syringe filters, Buchner funnels, fine frit filters, medium frit filters, centrifugal filter, sep-pack columns.

Without being bound by scientific theory, it is believed that substantially all dendrimer, which is sufficiently soluble in water, passes through any filtration device used and is part of the final composition. Therefore, it is assumed that all dendrimer used in the first step of the process for making the composition is part of the composition.

The method may comprise mixing resveratrol, dendrimer, and water to form a mixture comprising a dendrimer-resveratrol complex; and filtering the mixture to form the composition.

One embodiment of the method may include adding an excess of resveratrol (relative to dendrimer) to a solution of the dendrimer in water in a suitable container. To promote dissolution of the resveratrol, the mixture may be sonicated for up to about 10 seconds, about 20 seconds, about 30 seconds, about 40 seconds, about 50 seconds, about 60 seconds, about 2 minutes, about 3 minutes, about 4 minutes, or about 5 minutes. Sonication may be repeated up to about 2 times, about 3 times, about 4 times, or about 5 times. To further promote dissolution of the resveratrol, the mixture may be shaken up to about 5 minutes, about 10 minutes, about 15 minutes, about 20 minutes, about 30 minutes, about 40 minutes, about 50 minutes, about 1 hour, about 2 hours, about 3 hours, about 4 hours, about 5 hours, about 6 hours, about 7 hours, about 8 hours, about 9 hours, about 10 hours, about 11 hours, about 12 hours, about 14 hours, about 16 hours, about 18 hours, or about 24 hours. The mixture may be filtered (e.g., through a syringe filter) to form the composition.

The method may comprise mixing resveratrol, dendrimer, and water to form a mixture comprising a dendrimer-resveratrol complex; removing water after forming the mixture of the dendrimer-resveratrol complex to form a solid mixture; adding water to the solid mixture; and filtering the mixture to form the composition.

To generate a composition that improves the solubility of resveratrol and contains a therapeutically effective amount of resveratrol in the dendrimer-resveratrol complex, the resveratrol may be additionally solubilized in the process so that it may further contact and bind to the dendrimer. One method for further solubilizing the resveratrol in the initial mixture with dendrimer is by adding a solvent in addition to water. The additional solvent may be an organic solvent, such as a $C_1$-$C_4$ alcohol. A $C_1$-$C_4$ alcohol may include methanol, ethanol, propanol, butanol, or a combination thereof.

The method may comprise mixing resveratrol, dendrimer, and a solvent to form a mixture comprising a dendrimer-resveratrol complex; removing solvent after forming the mixture of the dendrimer-resveratrol complex to form a solid mixture; adding water to the solid mixture; and filtering the mixture to form the composition; wherein the solvent is a mixture of water and a $C_1$-$C_4$ alcohol.

Another embodiment of the method may include adding an excess of resveratrol (relative to dendrimer) to a solution of the dendrimer in water and methanol. To promote dissolution of the resveratrol, the mixture may be sonicated for up to about 10 seconds, about 20 seconds, about 30 seconds, about 40 seconds, about 50 seconds, about 60 seconds, about 2 minutes, about 3 minutes, about 4 minutes, or about 5 minutes. Sonication may be repeated up to about 2 times, about 3 times, about 4 times, or about 5 times. To further promote dissolution of the resveratrol, the mixture may be shaken up to about 5 minutes, about 10 minutes, about 15 minutes, about 20 minutes, about 30 minutes, about 40 minutes, about 50 minutes, about 1 hour, about 2 hours, about 3 hours, about 4 hours, about 5 hours, about 6 hours, about 7 hours, about 8 hours, about 9 hours, about 10 hours, about 11 hours, about 12 hours, about 14 hours, about 16 hours, about 18 hours, or about 24 hours. Solvent may be removed from the resulting solution via lyophilization to remove all water and methanol and form a solid mixture. Water may be added to the solid mixture. The mixture may be manually agitated, such as by the use of a shaker, to promote dissolution and dispersion of the solid. The mixture may be shaken up to about 5 minutes, about 10 minutes, about 15 minutes, about 20 minutes, about 30 minutes, about 40 minutes, about 50 minutes, about 1 hour, about 2 hours, about 3 hours, about 4 hours, about 5 hours, about 6 hours, about 7 hours, about 8 hours, about 9 hours, about 10 hours, about 11 hours, about 12 hours, about 14 hours, about 16 hours, about 18 hours, or about 24 hours. The mixture may be filtered (e.g., through a syringe filter) to form the composition.

The removal of solvent may include removal techniques such as evaporation, evaporation under reduced pressure, rotary evaporation, rotary evaporation under reduced pressure, sublimation, and lyophilization.

The solid mixture may be a powder, a sticky solid, a gum, an amorphous solid, a crystalline solid, an oil, a foam, or a combination thereof.

By adjusting the amount of the $C_1$-$C_4$ alcohol used in the method for making the composition, greater solubilities of the resveratrol associated with the resveratrol dendrimer complex of the composition may be achieved. A significant increase in solubility of the resveratrol may be achieved by using less than 50%, by volume, of the $C_1$-$C_4$ alcohol. By using less than 40%, by volume, of the $C_1$-$C_4$ alcohol, greater solubility of the resveratrol may be achieved. Specifically, by using less than 20%, by volume, of the $C_1$-$C_4$ alcohol, greater solubility of the resveratrol may be achieved. More specifically, by using less than 15%, by volume, of the $C_1$-$C_4$ alcohol, greater solubility of the resveratrol may be achieved. It was surprisingly discovered that methanol may be more effective than ethanol for enhancing solubility of the resveratrol. In particular, methanol may be more effective than ethanol for enhancing solubility of the resveratrol when used in an amount, by volume, of about 1% to about 50%, about 1% to about 50%, about 1% to about 45%, about 1% to about 40%, about 1% to about 35%, about 1% to about 30%, about 1% to about 25%, about 1% to about 20%, about 5% to about 15%, about 1% to about 10%, about 1% to about 5%, about 5% to about 50%, about 5% to about 45%, about 5% to about 40%, about 5% to about 35%, about 5% to about 30%, about 5% to about 25%, about 5% to about 20%, about 5% to about 15%, or about 5% to about 10%.

The solvent may comprise less than about 50%, by volume, the $C_1$-$C_4$ alcohol. The solvent may comprise less than about 49%, less than about 48%, less than about 47%, less than about 46%, less than about 45%, less than about 44%, less than about 43%, less than about 42%, less than about 41%, less than about 40%, less than about 39%, less than about 38%, less than about 37%, less than about 36%, less than about 35%, less than about 34%, less than about 33%, less than about 32%, less than about 31%, less than about 30%, less than about 29%, less than about 28%, less than about 27%, less than about 26%, less than about 25%, less than about 24%, less than about 23%, less than about 22%, less than about 21%, less than about 20%, less than about 19%, less than about 18%, less than about 17%, less than about 16%, less than about 15%, less than about 14%, less than about 13%, less than about 12%, less than about 11%, less than about 10%, less than about 9%, less than about 8%, less than about 7%, less than about 6%, or less than about 5%, by volume, the $C_1$-$C_4$ alcohol. The solvent may comprise at least about 1%, at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, at least about 15%, at least about 16%, at least about 17%, at least about 18%, at least about 19%, at least about 20%, at least about 25%, at least about 30%, at least about 35%, at least about 40%, or at least about 45%, by volume, the $C_1$-$C_4$ alcohol. The solvent may comprise about 5% to about 50%, about 10% to about 50%, about 15% to about 50%, about 20% to about 50%, about 25% to about 50%, about 30% to about 50%, about 35% to about 50%, about 40% to about 50%, about 45% to about 50%, about 5% to about 10%, about 5% to about 15%, about 5% to about 20%, about 5% to about 25%, about 5% to about 30%, about 5% to about 35%, about 5% to about 40%, about 5% to about 45%, about 10% to about 15%, about 10% to about 20%, about 10% to about 25%, about 10% to about 30%, about 10% to about 35%, about 10% to about 40%, about 10% to about 45%, about 15% to about 20%, about 15% to about 25%, about 15% to about 30%, about 15% to about 35%, about 15% to about 40%, about 15% to about 45%, about 20% to about 25%, about 20% to about 30%, about 20% to about 35%, about 20% to about 40%, about 20% to about 45%, about 25% to about 30%, about 25% to about 35%, about 25% to about 40%, about 25% to about 45%, about 30% to about 35%, about 30% to about 40%, about 30% to about 45%, about 35% to about 40%, about 35% to about 45%, or about 40% to about 45%, by volume, the $C_1$-$C_4$ alcohol.

The solvent may comprise about 49%, about 48%, about 47%, about 46%, about 45%, about 44%, about 43%, about 42%, about 41%, about 40%, about 39%, about 38%, about 37%, about 36%, about 35%, about 34%, about 33%, about 32%, about 31%, about 30%, about 29%, about 28%, about 27%, about 26%, about 25%, about 24%, about 23%, about 22%, about 21%, about 20%, about 19%, about 18%, about 17%, about 16%, about 15%, about 14%, about 13%, about 12%, about 11%, about 10%, about 9%, about 8%, about 7%, about 6%, or about 5%, by volume, the $C_1$-$C_4$ alcohol.

The solvent may comprise less than about 50%, by volume, methanol. The solvent may comprise less than about 49%, less than about 48%, less than about 47%, less than about 46%, less than about 45%, less than about 44%, less than about 43%, less than about 42%, less than about 41%, less than about 40%, less than about 39%, less than about 38%, less than about 37%, less than about 36%, less than about 35%, less than about 34%, less than about 33%, less than about 32%, less than about 31%, less than about 30%, less than about 29%, less than about 28%, less than about 27%, less than about 26%, less than about 25%, less than about 24%, less than about 23%, less than about 22%, less than about 21%, less than about 20%, less than about 19%, less than about 18%, less than about 17%, less than about 16%, less than about 15%, less than about 14%, less than about 13%, less than about 12%, less than about 11%, less than about 10%, less than about 9%, less than about 8%, less than about 7%, less than about 6%, or less than about 5%, by volume, methanol. The solvent may comprise at least about 1%, at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, at least about 15%, at least about 16%, at least about 17%, at least about 18%, at least about 19%, at least about 20%, at least about 25%, at least about 30%, at least about 35%, at least about 40%, or at least about 45%, by volume, methanol. The solvent may comprise about 5% to about 50%, about 10% to about 50%, about 15% to about 50%, about 20% to about 50%, about 25% to about 50%, about 30% to about 50%, about 35% to about 50%, about 40% to about 50%, about 45% to about 50%, about 5% to about 10%, about 5% to about 15%, about 5% to about 20%, about 5% to about 25%, about 5% to about 30%, about 5% to about 35%, about 5% to about 40%, about 5% to about 45%, about 10% to about 15%, about 10% to about 20%, about 10% to about 25%, about 10% to about 30%, about 10% to about 35%, about 10% to about 40%, about 10% to about 45%, about 15% to about 20%, about 15% to about 25%, about 15% to about 30%, about 15% to about 35%, about 15% to about 40%, about 15% to about 45%, about 20% to about 25%, about 20% to about 30%, about 20% to about 35%, about 20% to about 40%, about 20% to about 45%, about 25% to about 30%, about 25% to about 35%, about 25% to about 40%, about 25% to about 45%, about 30% to about 35%, about 30% to about 40%, about 30% to about 45%, about 35% to about 40%, about 35% to about 45%, or about 40% to about 45%, by volume, methanol.

The solvent may comprise about 49%, about 48%, about 47%, about 46%, about 45%, about 44%, about 43%, about 42%, about 41%, about 40%, about 39%, about 38%, about 37%, about 36%, about 35%, about 34%, about 33%, about 32%, about 31%, about 30%, about 29%, about 28%, about 27%, about 26%, about 25%, about 24%, about 23%, about 22%, about 21%, about 20%, about 19%, about 18%, about 17%, about 16%, about 15%, about 14%, about 13%, about 12%, about 11%, about 10%, about 9%, about 8%, about 7%, about 6%, or about 5%, by volume, methanol.

The solvent may further comprise water. The balance may be water.

A. Embodiments of the Method for Preparing the Composition

In an embodiment, the method may comprise mixing resveratrol, dendrimer, and solvent to form a mixture comprising a dendrimer-resveratrol complex; removing solvent after forming the mixture of the dendrimer-resveratrol complex to form a solid mixture; adding water to the solid mixture; and filtering the mixture to form the composition; wherein the solvent is a mixture of water and methanol.

In an embodiment, the method may comprise mixing resveratrol, dendrimer, and solvent to form a mixture comprising a dendrimer-resveratrol complex; removing solvent after forming the mixture of the dendrimer-resveratrol complex to form a solid mixture; adding water to the solid mixture; and filtering the mixture to form the composition; wherein the solvent is a mixture of water and ethanol.

In an embodiment, the method may comprise mixing resveratrol, dendrimer, and solvent to form a mixture comprising a dendrimer-resveratrol complex; removing solvent after forming the mixture of the dendrimer-resveratrol complex to form a solid mixture; adding water to the solid mixture; and filtering the mixture to form the composition; wherein the solvent is a mixture of water and methanol; wherein the solvent comprises less than about 50%, by volume, methanol.

In an embodiment, the method may comprise mixing resveratrol, dendrimer, and solvent to form a mixture comprising a dendrimer-resveratrol complex; removing solvent after forming the mixture of the dendrimer-resveratrol complex to form a solid mixture; adding water to the solid mixture; and filtering the mixture to form the composition; wherein the solvent is a mixture of water and ethanol; wherein the solvent comprises less than about 50%, by volume, ethanol.

In an embodiment, the method may comprise mixing resveratrol, dendrimer, and solvent to form a mixture comprising a dendrimer-resveratrol complex; removing solvent after forming the mixture of the dendrimer-resveratrol complex to form a solid mixture; adding water to the solid mixture; and filtering the mixture to form the composition; wherein the solvent is a mixture of water and methanol; wherein the solvent comprises about 5% to about 20%, by volume, methanol.

In an embodiment, the method may comprise mixing resveratrol, dendrimer, and solvent to form a mixture comprising a dendrimer-resveratrol complex; removing solvent after forming the mixture of the dendrimer-resveratrol complex to form a solid mixture; adding water to the solid mixture; and filtering the mixture to form the composition; wherein the solvent is a mixture of water and ethanol; wherein the solvent comprises about 5% to about 20%, by volume, ethanol.

In an embodiment, the method may comprise mixing resveratrol, dendrimer, and solvent to form a mixture comprising a dendrimer-resveratrol complex; removing solvent after forming the mixture of the dendrimer-resveratrol complex to form a solid mixture; adding water to the solid mixture; and filtering the mixture to form the composition; wherein the solvent is a mixture of water and methanol; wherein the solvent comprises about 10%, by volume, methanol.

In an embodiment, the method may comprise mixing resveratrol, dendrimer, and solvent to form a mixture comprising a dendrimer-resveratrol complex; removing solvent after forming the mixture of the dendrimer-resveratrol complex to form a solid mixture; adding water to the solid mixture; and filtering the mixture to form the composition; wherein the solvent is a mixture of water and ethanol; wherein the solvent comprises about 10%, by volume, ethanol.

In an embodiment, the method may comprise mixing resveratrol, dendrimer, and solvent to form a mixture comprising a dendrimer-resveratrol complex; removing solvent after forming the mixture of the dendrimer-resveratrol complex to form a solid mixture; adding water to the solid mixture; and filtering the mixture to form the composition; wherein the solvent is a mixture of water and methanol; wherein the solvent comprises about 5%, by volume, methanol.

In an embodiment, the method may comprise mixing resveratrol, dendrimer, and solvent to form a mixture comprising a dendrimer-resveratrol complex; removing solvent after forming the mixture of the dendrimer-resveratrol complex to form a solid mixture; adding water to the solid mixture; and filtering the mixture to form the composition; wherein the solvent is a mixture of water and ethanol; wherein the solvent comprises about 5%, by volume, ethanol.

In an embodiment, the method may comprise mixing resveratrol, dendrimer, and solvent to form a mixture comprising a dendrimer-resveratrol complex; removing solvent after forming the mixture of the dendrimer-resveratrol complex to form a solid mixture; adding water to the solid mixture; and filtering the mixture to form the composition; wherein the solvent is a mixture of water and methanol; wherein the solvent comprises about 10%, by volume, methanol; wherein the composition comprises a dendrimer-resveratrol complex, the composition being essentially free of organic solvent; wherein the composition comprises water; wherein the pH of the composition is about 7; wherein at least 95%, by weight, of the resveratrol in the composition is associated with the dendrimer; wherein the aqueous solubility of the resveratrol associated with the dendrimer is at least 40 times greater than the aqueous solubility of neat resveratrol; wherein the resveratrol associated with the dendrimer degrades less than 10% after 4 days at ambient temperature; wherein at least 50%, by weight, of the resveratrol associated with dendrimer permeates the skin in 20 minutes or less in a transdermal permeation study utilizing Franz Diffusion Cells and rat skin samples; the composition comprising about 1.0 mM dendrimer or less.

In an embodiment, the method may comprise mixing resveratrol, dendrimer, and solvent to form a mixture comprising a dendrimer-resveratrol complex; removing solvent after forming the mixture of the dendrimer-resveratrol complex to form a solid mixture; adding water to the solid mixture; and filtering the mixture to form the composition; wherein the solvent is a mixture of water and methanol; wherein the solvent comprises about 10%, by volume, methanol; wherein the composition comprises a dendrimer-resveratrol complex, the composition being essentially free of organic solvent; wherein the composition comprises water; wherein the pH of the composition is about 7; wherein at least 95%, by weight, of the resveratrol in the composition is associated with the dendrimer; wherein the aqueous solubility of the resveratrol associated with the dendrimer is at least 40 times greater than the aqueous solubility of neat resveratrol; wherein the resveratrol associated with the dendrimer degrades less than 10% after 4 days at ambient temperature; wherein at least 50%, by weight, of the resveratrol associated with dendrimer permeates the skin in 20 minutes or less in a transdermal permeation study utilizing Franz Diffusion Cells and rat skin samples; the composition comprising about 0.40 mM dendrimer or less.

In an embodiment, the method may comprise mixing resveratrol, dendrimer, and solvent to form a mixture comprising a dendrimer-resveratrol complex; removing solvent after forming the mixture of the dendrimer-resveratrol complex to form a solid mixture; adding water to the solid mixture; and filtering the mixture to form the composition; wherein the solvent is a mixture of water and methanol; wherein the solvent comprises about 10%, by volume, methanol; wherein the composition comprises a dendrimer-resveratrol complex, the composition being essentially free of organic solvent; wherein the composition comprises water; wherein the pH of the composition is about 7; wherein at least 95%, by weight, of the resveratrol in the composition is associated with the dendrimer; wherein the aqueous solubility of the resveratrol associated with the dendrimer is at least 40 times greater than the aqueous solubility of neat resveratrol; wherein the resveratrol associated with the dendrimer degrades less than 10% after 4 days at ambient temperature; wherein at least 50%, by weight, of the resveratrol associated with dendrimer permeates the skin in 20 minutes or less in a transdermal permeation study utilizing Franz Diffusion Cells and rat skin samples; the composition comprising about 1.0 mM dendrimer or less; wherein the dendrimer is PAMAM G4-amine dendrimer.

In an embodiment, the method may comprise mixing resveratrol, dendrimer, and solvent to form a mixture comprising a dendrimer-resveratrol complex; removing solvent after forming the mixture of the dendrimer-resveratrol complex to form a solid mixture; adding water to the solid mixture; and filtering the mixture to form the composition; wherein the solvent is a mixture of water and methanol; wherein the solvent comprises about 10%, by volume, methanol; the composition may comprise a dendrimer-resveratrol complex, the composition being essentially free of organic solvent; wherein the composition comprises water; wherein the pH of the composition is about 7; wherein at least 95%, by weight, of the resveratrol in the composition is associated with the dendrimer; wherein the aqueous solubility of the resveratrol associated with the dendrimer is at least 40 times greater than the aqueous solubility of neat resveratrol; wherein the resveratrol associated with the dendrimer degrades less than 10% after 4 days at ambient temperature; wherein at least 50%, by weight, of the resveratrol associated with dendrimer permeates the skin in 20 minutes or less in a transdermal permeation study utilizing Franz Diffusion Cells and rat skin samples; the composition comprising about 0.40 mM dendrimer or less; wherein the dendrimer is PAMAM G4-amine dendrimer.

In an embodiment, the method may also include a final step wherein the composition is dried to a solid form.

The removal of solvent may include removal techniques such as evaporation, evaporation under reduced pressure, rotary evaporation, rotary evaporation under reduced pressure, sublimation, evaporation with stirring and lyophilization. The solid mixture may be a powder, a sticky solid, a gum, an amorphous solid, a crystalline solid, an oil, a foam, or a combination thereof.

4. Pharmaceutical Compositions

The disclosure is further directed to pharmaceutical compositions. The pharmaceutical compositions may comprise the compositions set forth herein, as well as one or more pharmaceutically acceptable carrier, and/or adjuvants. The pharmaceutically acceptable carrier is non-toxic. The pharmaceutical compositions can be formulated for any type of administration, including, but not limited to, oral administration in solid or liquid form, for parenteral injection or for topical administration.

A. Pharmaceutically Acceptable Carriers

The pharmaceutically acceptable carrier may be an inert solid, semi-solid or liquid filler, diluent, encapsulating material or formulation auxiliary of any type.

The pharmaceutically acceptable carrier may be a natural or a man-made carrier. A natural pharmaceutical carrier requires no chemical or biological manipulation into a carrier state. Some examples of materials which can serve as natural pharmaceutically acceptable carriers are sugars such as lactose, glucose and sucrose; starches such as corn starch and potato starch; cellulose; powdered tragacanth; malt; gelatin; talc; cocoa butter and suppository waxes; oils such as peanut oil, cottonseed oil, safflower oil, sesame oil, olive oil, corn oil and soybean oil; glycols; agar; alginic acid; pyrogen-free water; isotonic saline; Ringer's solution; ethyl alcohol; phosphate buffer solutions, and antioxidants can also be present in the composition, according to the judgment of one skilled in the art of formulations The pharmaceutically acceptable carrier may be a synthesized man-made carrier. Some examples of synthesized pharmaceutically acceptable carriers may be cellulose derivatives such as sodium carboxymethyl cellulose, ethyl cellulose and cellulose acetate; propylene glycol; esters such as ethyl oleate and ethyl laurate; buffering agents such as magnesium hydroxide and aluminum hydroxide, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of one skilled in the art of formulations B. Administration The pharmaceutical compositions of can be administered to humans and other mammals orally, rectally, parenterally, intracisternally, intravaginally, intraperitoneally, ocularly, topically (as by powders, ointments or drops), bucally or as an oral or nasal spray. The term "parenterally", as used herein, refers to modes of administration which include intravenous, intramuscular, intraperitoneal, intrasternal, subcutaneous, intraarticular injection and infusion.

Pharmaceutical compositions for parenteral injection comprise pharmaceutically acceptable sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propylene glycol, polyethylene glycol, glycerol, and the like, and suitable mixtures thereof), vegetable oils (such as olive oil) and injectable organic esters such as ethyl oleate, or suitable mixtures thereof. Suitable fluidity of the composition may be maintained, for example, by the use of a coating such as lecithin, by the maintenance of the required particle size in the case of dispersions, and by the use of surfactants.

These compositions may also contain adjuvants such as preservative agents, wetting agents, emulsifying agents, and dispersing agents. Prevention of the action of microorganisms may be ensured by various antibacterial and antifungal agents, for example, parabens, chlorobutanol, phenol, sorbic acid, and the like. It may also be desirable to include isotonic agents, for example, sugars, sodium chloride and the like. Prolonged absorption of the injectable pharmaceutical form may be brought about by the use of agents delaying absorption, for example, aluminum monostearate and gelatin.

1) Solid Dose Pharmaceutical Compositions

The pharmaceutical composition may be a solid dose formulation. Solid dosage forms for oral administration include capsules, tablets, pills, powders, and granules. In such solid dosage forms, one or more compositions of the disclosure is mixed with at least one inert pharmaceutically acceptable carrier such as sodium citrate or dicalcium phosphate and/or a) fillers or extenders such as starches, lactose, sucrose, glucose, mannitol, and salicylic acid; b) binders such as carboxymethylcellulose, alginates, gelatin, polyvinylpyrrolidinone, sucrose, and acacia; c) humectants such as glycerol; d) disintegrating agents such as agar-agar, calcium carbonate, potato or tapioca starch, alginic acid, certain silicates, and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay; and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using lactose or milk sugar as well as high molecular weight polyethylene glycols.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract in a delayed manner. Examples of materials which can be useful for delaying release of the active agent can include polymeric substances and waxes.

2) Topical/Transdermal Pharmaceutical Compositions

The pharmaceutical composition may be in the form of a topical or transdermal composition. Dosage forms for topical or transdermal administration of the composition include ointments, pastes, creams, lotions, gels, powders, solutions, sprays, inhalants or patches. A desired composition of the disclosure is admixed under sterile conditions with a pharmaceutically acceptable carrier and any needed preservatives or buffers as may be required. Ophthalmic formulation, ear drops, eye ointments, powders and solutions are also contemplated as being within the scope of this disclosure.

The ointments, pastes, creams and gels may contain, in addition to an active composition of this disclosure, animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compositions of this disclosure, lactose, talc, silicic acid, aluminum hydroxide, calcium silicates and polyamide powder, or mixtures of these substances. Sprays can additionally contain customary propellants such as chlorofluorohydrocarbons.

Dosage forms for topical administration of a composition of this disclosure include powders, sprays, ointments and inhalants. The active composition is mixed under sterile conditions with a pharmaceutically acceptable carrier and any needed preservatives, buffers or propellants, which can be required. Ophthalmic formulations, eye ointments, powders and solutions are contemplated as being within the scope of this disclosure. Aqueous liquid compositions comprising compositions of the disclosure also are contemplated.

5. Methods of Using the Composition

The present disclosure also includes methods for treating and/or preventing disorders, diseases, or conditions by administering the compositions or pharmaceutical compositions described herein to a subject in need thereof. This includes treatment and/or prevention of disorders or conditions that can be treated or prevented by administration of resveratrol. In other words, administration of a composition or pharmaceutical composition described herein to a subject in need thereof may provide for curative treatment of such a disorder or condition, control the progression of such a disorder or condition, ameliorate the symptoms associated with such a disorder or condition, and/or reduce the risk for such a disorder or condition.

The pharmaceutical composition may be useful for treating and preventing certain disorders or conditions in humans and animals. Typically, treatment or prevention of such disorders or conditions can be effected by administering a composition of the disclosure, either alone or in combination with another active agent as part of a therapeutic regimen to a subject in need thereof.

The compositions and pharmaceutical compositions may be used to treat and/or prevent cancer, cardiovascular disease, cardiac failure, diabetes, Alzheimer's disease, Parkinson's disease and other brain diseases, fatty liver disease, obesity, cataracts, osteoporosis, muscle wasting, sleep disorders, acoustic trauma, inflammatory disease, psoriasis, arthritis, colitis, aging, viral disease, reproductive disease, and skin conditions or disorders.

Examples of skin conditions or disorders include skin cancer, hyperpigmentation, inflammation, burns, psoriasis, eczema, cellulitis, hives, dermatitits, acne, aging, UV light mediated aging, an inflammatory disorder, or a hyperproliferative disorder.

To treat and/or prevent skin conditions or disorders such as those listed above, the pharmaceutical composition may be topically administered to the skin or mucous membrane.

A. General Dosage Regimens

When used in the above or other treatments, a therapeutically effective amount of one of the compositions disclosed can be employed. The phrase "therapeutically effective amount" of the composition of the disclosure means a sufficient amount of the composition to bring about a desired in vivo effect and treat disorders or conditions, at a reasonable benefit/risk ratio applicable to any medical treatment. It will be understood, however, that the total daily usage of the compounds and compositions of the disclosure will be decided by the attending physician within the scope of sound medical judgment. The specific therapeutically effective dose level for any particular patient will depend upon a variety of factors including the disorder being treated and the severity of the disorder; activity of the specific compound and/or composition employed; the specific compound and/or composition employed; the age, body weight, general health, sex and diet of the patient; the time of administration, route of administration, and rate of excretion of the specific compound and/or composition employed; the duration of the treatment; drugs used in combination or coincidental with the specific compound and/or composition employed; and like factors well known in the medical arts. For example, it is well within the skill of the art to start doses of the compound and/or composition at levels lower than required to achieve the desired therapeutic effect and to gradually increase the dosage until the desired effect is achieved.

The pharmaceutical composition can be between 1 µg to 10 mg active component/kg body weight/time and can be 20 µg to 10 mg component/kg body weight/time. The pharmaceutical composition can be administered every 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days. The pharmaceutical doses for effective treatment can be 1, 2, 3, 4, 5, 6, 7, 8, 9, 10, or more doses.

B. Combination Therapies

The composition comprising the dendrimer-resveratrol complex as described above may be used in combination with one or more other drugs in the treatment, prevention, control, amelioration, or reduction of risk of disorders or conditions for which the composition or the other drugs may have utility as described above, where the combination of the drugs together are safer or more effective than either drug alone. Such other drug(s) may be administered, by a route and in an amount commonly used therefore, contemporaneously or sequentially with the composition. When the composition is used contemporaneously with one or more other drugs, a pharmaceutical composition in unit dosage form containing such other drugs and the composition is preferred. However, the combination therapy may also include therapies in which the composition and one or more other drugs are administered on different overlapping schedules. It is also contemplated that when used in combination with one or more other active ingredients, the compositions of the present disclosure and the other active ingredients may be used in lower doses than when each is used singly. Accordingly, the pharmaceutical compositions of the present disclosure include those that contain one or more other active ingredients, in addition to the composition comprising the dendrimer-resveratrol complex. The above combinations include combinations of a composition of the present disclosure not only with one other active compound, but also with two or more other active compounds. For example, the composition can be combined with a variety of different anti-cancer drugs such as chemotherapeutics, anti-tumor agents, and anti-proliferative agents, such as fluorouracil, imiquimod, vismodegib, aldesleukin, dacarbazine, vemurafenib (Zelboraf), and ipilimumab.

The weight ratio of the composition of the present disclosure to the second active ingredient may be varied and will depend upon the effective dose of each ingredient. Generally, an effective dose of each will be used. Thus, for example, when a composition of the present disclosure is combined with another agent, the weight ratio of the composition of the present disclosure to the other agent will generally range from about 1000:1 to about 1:1000, preferably about 200:1 to about 1:200. Combinations of a composition of the present disclosure and other active ingredients will generally also be within the aforementioned range, but in each case, an effective dose of each active ingredient should be used.

The compositions and processes of the disclosure will be better understood by reference to the following examples, which are intended as an illustration of and not a limitation upon the scope of the disclosure.

EXAMPLES

Formulations of the dendrimer-resveratrol complexes are referred to herein as a weight/volume %. This weight/volume % is defined as milligram (mg) of dendrimer per total microliters (µL) of the formulation. For example, the 1% formulation comprises 10 mg in 1,000 µL, and the 0.1% formulation comprises 1 mg in 1,000 µL. The 1% formulation has a dendrimer concentration of 0.70 mM, and the 0.1% formulation has a dendrimer concentration of 0.07 mM.

Example 1. HPLC Analysis of Resveratrol

An HPLC method for the determination of resveratrol concentration was developed using a Dionex UltiMate® 3000 HPLC and an RP-C18 column. Resveratrol (drug) was eluted through the column with 60% water and 40% methanol followed by UV detection at 308 nm ($\tilde{\lambda}_{max}$ of the trans form of resveratrol).

Example 2. Formulation of PAMAM Dendrimer-Resveratrol Complex (PAMAM-Resveratrol)

Screening Phase: Amine, carboxylate, and TRIS PAMAM dendrimers were tested at both pH 7 and pH 5. Each was tested at a 1% w/v concentration in Millipore water using protocol 1 (below). Further testing was done on a PAMAM G4-Amine dendrimer (pH 7).

Protocol 1 (1% w/v formulation): 2 mg of resveratrol (an excess) was added to vials containing a total volume of 1 mL, made of a combination of 10 mg PAMAM dendrimer and Millipore water in varying fractions. Each vial was sonicated for 30 seconds in three 10-second increments, placed in an orbital shaker, and shaken at ambient temperature overnight. The suspensions were filtered through a 0.2 µm nylon syringe filter and analyzed for dendrimer-associated resveratrol by HPLC/UV spectroscopy at 308 nm.

Protocol 2 (1% w/v formulation): 5 mg of resveratrol (an excess) was added to vials containing 500 µL methanol, and this formulation was added drop-wise to vials containing 400 PAMAM G4-Amine dendrimer (10 mg) (pH 7) and 600 µL Millipore water. Control samples (containing no PAMAM G4-Amine dendrimer (pH 7) and 1000 µL Millipore water) were also prepared. Each formulation was sonicated for 2 minutes in four 30-second increments and then placed in an orbital shaker and shaken at ambient temperature overnight. Vials underwent lyophilization to remove water and methanol, and were reconstituted with 1000 Millipore water. Formulations were placed in an orbital shaker at ambient temperature and shaken for 4 hours. The suspensions were then filtered through a 0.2 µm nylon syringe filter and analyzed for dendrimer-associated drug by HPLC/UV spectroscopy at 308 nm.

Modified Protocol 2 (1% w/v formulation): Protocol 2 was modified further to reduce the preparation time. In an effort to improve efficacy of the dendrimer-resveratrol formulations and minimize resveratrol degradation during the preparation process, the method of preparation Protocol 2 (described above) was slightly altered. In the modified protocol, the preparations were shaken for a period of 3-4 hours prior to lyophilization (as opposed to overnight) and the formulations were protected from light throughout preparation by means of aluminum foil.

0.1% w/v Dendrimer Formulations: An examination was made into the effect that a decreased amount of PAMAM dendrimer would have on resveratrol solubility in water. These formulations were prepared according to Protocol 1 and the modified Protocol 2. Each formulation contained 1 mg PAMAM amine dendrimer as opposed to 10 mg PAMAM amine dendrimer used in the 1% w/v preparations described above. The method of preparation is otherwise identical between the 1% and 0.1% formulations.

pH 2.5 Formulations: An examination of the effect of pH on the solubility of resveratrol in the PAMAM dendrimer formulations was approached in two ways. Two 0.1% dendrimer formulations were created according to modified Protocol 2. In the first formulation, HCl was used to lower the pH of the PAMAM amine dendrimer to 2.5 prior to the introduction of resveratrol to make a formulation. In the second formulation the pH of dendrimer-resveratrol prepared at pH 7.0 was lowered to 2.5. Additionally, a control formulation of resveratrol in water with the pH lowered to 2.5 was analyzed.

Figure 3:
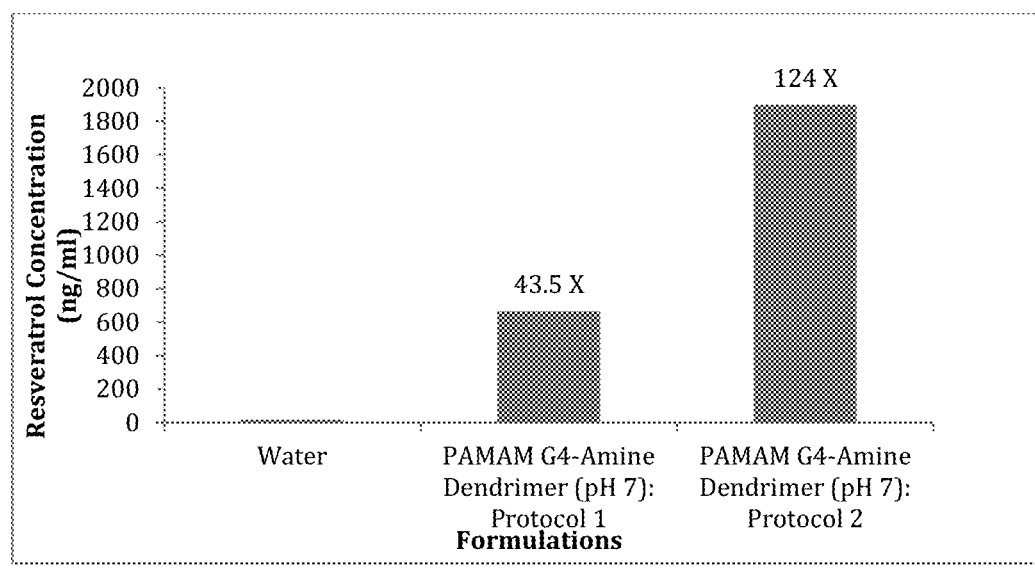
FIG. 3 is a graph depicting dendrimer mediated aqueous solubility enhancement of resveratrol.

Nanosuspension Formulation: A nanosuspension of resveratrol in water was created using a procedure based on modified Protocol 2. A 0.1% PAMAM-G4 amine dendrimer-resveratrol formulation was created, to which 1 drop (16 mg) of TWEEN 80 was added. The formulation was then sonicated and shaken in an orbital shaker for 3 hours before being lyophilized. After lyophilization, the formulation was reconstituted with 500 uL of water and shaken for an additional 3 hours before being filtered and analyzed via HPLC. Throughout preparation, the formulation was protected from light by means of aluminum foil Example 3. Solubility Studies PAMAM G4-Amine, PAMAM-G4-OH and PAMAM G3.5-COOH dendrimers were used to prepare resveratrol formulations. Of the three dendrimers, PAMAM G4-Amine dendrimer (1% w/v formulation) enhanced water solubility of neat resveratrol from 43.5 to 124 fold using protocols 1 and 2 (FIG. 3). PAMAM-G4-OH and PAMAM-G3.5-COOH dendrimers did not show any water solubility enhancement of resveratrol.

Solubility Profile of PAMAM G4 Amine Dendrimer: A solubility profile was also created with different concentrations of PAMAM G4-Amine dendrimer (pH 7) in water using Protocol 1. The dendrimer concentrations used were 0, 0.25, and 1 mg/mL. An increase in the concentration of resveratrol associated with the dendrimer (solubility) was observed with an increase in PAMAM G4-Amine dendrimer used in the formulation at pH 7.

Figure 4:
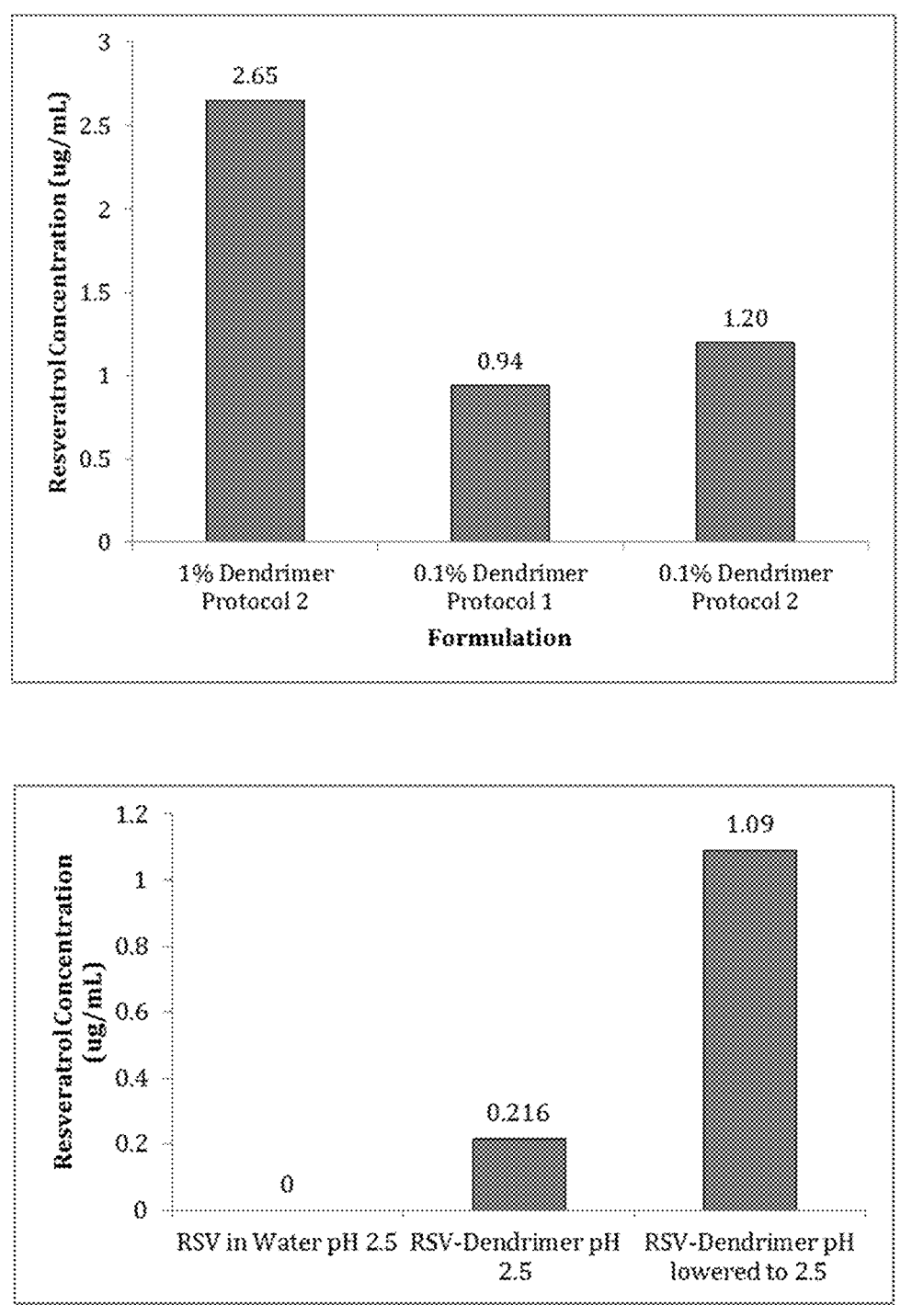

Comparison of formulations: HPLC analysis of the 0.1% PAMAM-G4 amine dendrimer-resveratrol formulations measured resveratrol concentrations of 0.94 ug/mL (0.004 mM) (Protocol 1) and 1.20 ug/mL (0.005 mM) (Modified Protocol 2), while a 1% PAMAM-G4 amine dendrimer-resveratrol formulation following modified Protocol 2 gave a resveratrol concentration of 2.65 ug/mL (0.011 mM) (FIG. 4—upper). No degradation of resveratrol was observed with any of these formulations.

Effect of lowering pH on solubility: A formulation containing 0.1% PAMAM amine dendrimer lowered to pH 2.5 before the addition of resveratrol was found to contain 0.216 ug/mL (0.0009 mM) resveratrol when measured by HPLC. This is lower than the resveratrol loading achieved at pH 7. When the resveratrol was added to the dendrimer formulation prior to lowering the pH, a greater resveratrol concentration was recorded, 1.09 ug/mL (0.005 mM). Both of these results show an improvement over the control of resveratrol in water adjusted to pH 2.5 alone, in which no resveratrol solubility was detected (FIG. 4—lower). This indicates that resveratrol complexed to dendrimer can be protected in the harsh acidic conditions of the gastrointestinal tract.

Comparison of Organic Solvents and Initial Organic Solvent Content: After initial HPLC measurements using 33.3% methanol (v/v) as an organic solvent (see protocol 2 above), resveratrol solubility was examined using two organic solvents (methanol and ethanol; 10.0% and 62.5%). The basic procedure used was similar to Protocol 2 in the initial solubility studies. For each of the organic solvents, four formulations were prepared. The first was a control formulation containing 5 mg resveratrol, 500 μL of the organic solvent, 1000 μL Millipore water, and no dendrimer. A 10% organic solvent formulation was prepared with 5 mg resveratrol, 500 μL organic solvent, 4200 μL Millipore water and 300 μL (0.0093 g) PAMAM G4-Amine dendrimer (pH 7). The 33.3% organic solvent formulation was prepared using 5 mg resveratrol, 500 μL organic solvent, 700 μL Millipore water, and 300 μL PAMAM G4-Amine dendrimer (pH 7). The final, 62.5%, formulation consisted of 5 mg resveratrol, 500 μL organic solvent, and 300 μL PAMAM G4-Amine dendrimer (pH 7).

Each formulation was sonicated for 2 minutes in 30-second increments (four times) and placed in an orbital shaker overnight at ambient temperature. Formulations then underwent lyophilization to remove all water and organic solvent and were reconstituted with 1000 Millipore water. Formulations were placed in an orbital shaker for 4 hours at ambient temperature and then filtered through a 0.2 μm nylon syringe filter and analyzed or dendrimer-associated drug by HPLC/UV spectroscopy at 308 nm.

Figure 5:
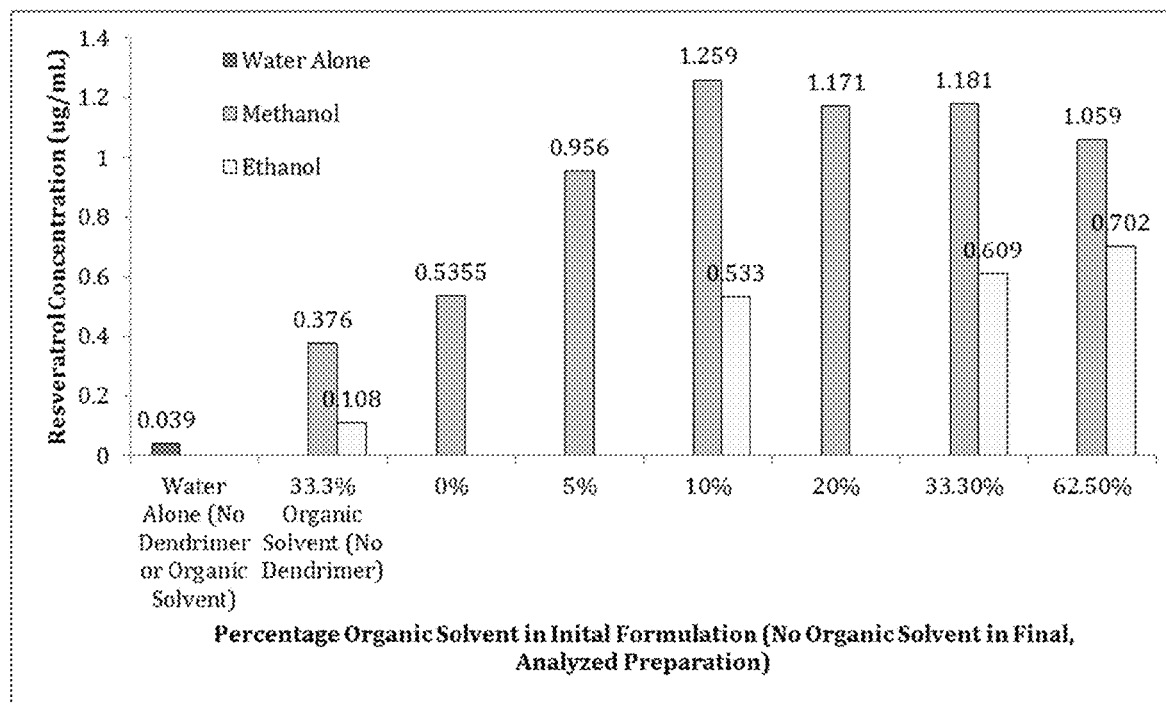
FIG. 5 is a series of graphs depicting the effect of organic solvent and initial concentration of the organic solvent on resveratrol solubility associated with 1% PAMAM G4-amine dendrimer-resveratrol formulations (upper); and the effect of initial methanol concentration on resveratrol solubility associated with 1% PAMAM G4-amine dendrimer-resveratrol formulations (lower).
Figure 5:
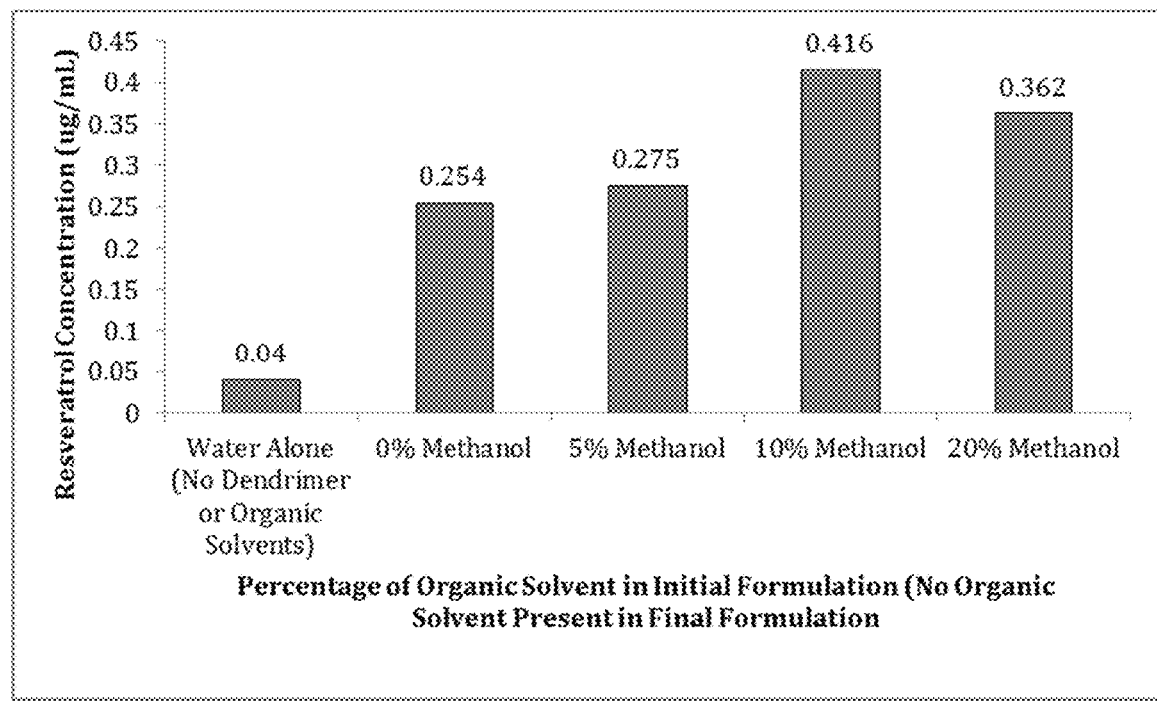

Surprisingly, methanol was more effective than ethanol to enhance resveratrol solubility in water by dendrimer (FIG. 5—upper). Unexpectedly, methanol is more effective at lower concentrations (10%) compared to the higher concentrations (33.3% and 62.5%) in a 1% G4 amine dendrimer formulation. A similar trend is seen when the dendrimer formulations contain only 0.1% PAMAM-G4 amine dendrimer, with 10% methanol again producing the greatest enhancement (FIG. 5—lower).

Nanosuspension Formulation: HPLC analysis of the 0.1% PAMAM-G4 amine dendrimer-resveratrol nanosuspension resulted in a resveratrol concentration of 3.59 mg/mL (0.016 mM), roughly a 1000-fold increase over previous formulations.

Example 4. Stability Studies

The ability of PAMAM dendrimers to enhance the stability of resveratrol in aqueous solution was also evaluated. Stability was determined by HPLC analysis of a 1% PAMAM-G4 amine dendrimer-resveratrol complex at 21° C. (ambient temperature), 37° C., and 4° C. Concentrations were analyzed initially (day 0) and on day 4, 11, and 22.

Figure 6:
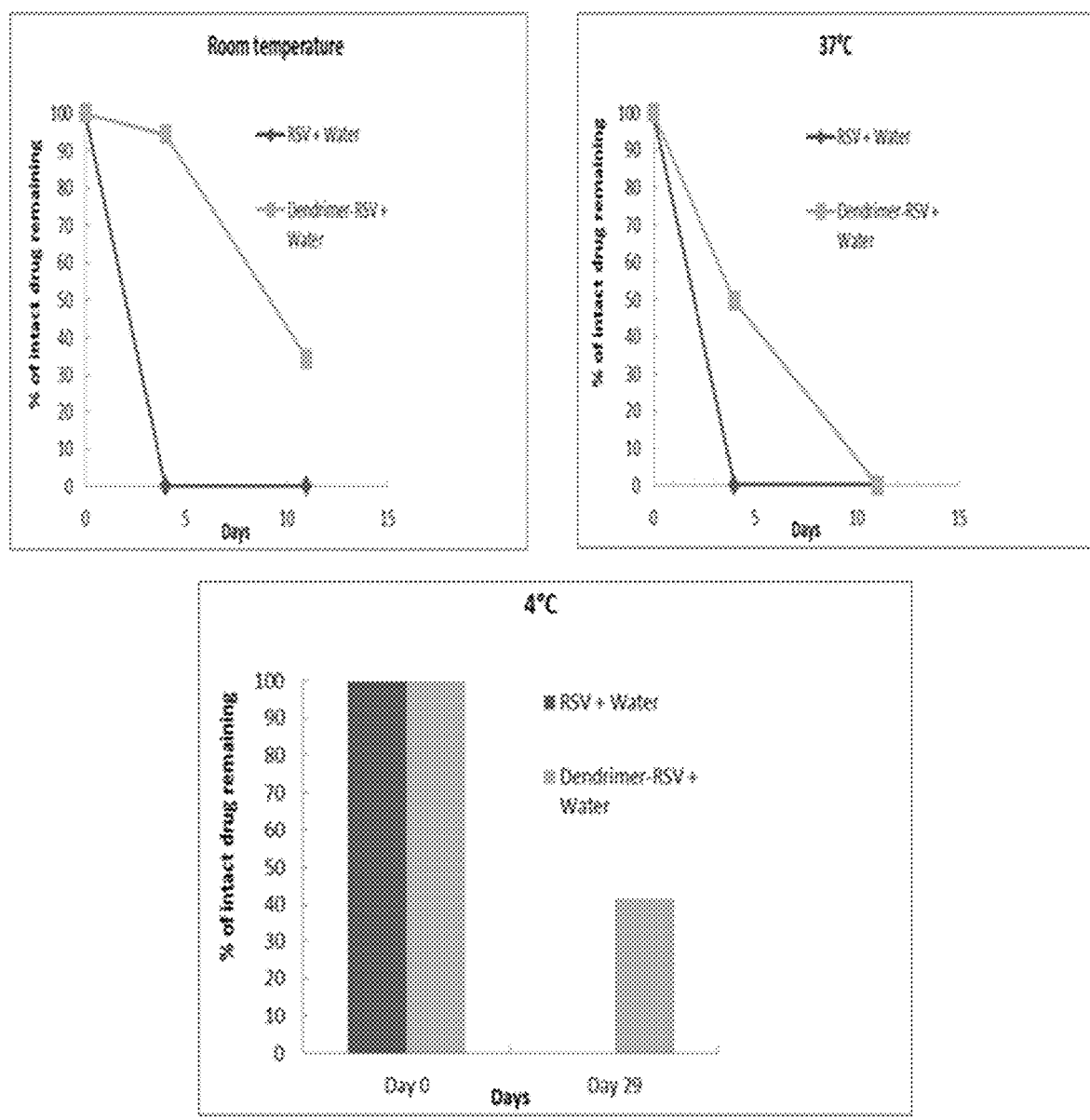
FIG. 6 is a series of graphs depicting the stability of PAMAM G4-amine dendrimer-resveratrol formulations and resveratrol at a series of temperatures.

A possible mechanism of action for increased stability involves resveratrol entrapment within the dendrimer nanostructure, thus preventing solvent exposure and minimizing degradation in aqueous solution. At ambient temperature, the aqueous resveratrol control solution (no dendrimer) was completely degraded by day 4, whereas 94.4% resveratrol remained intact with PAMAM G4-Amine dendrimer (pH 7) under identical conditions (FIG. 6—upper left). At 4° C., resveratrol was monitored on day 0 and day 29, and no drug remained with the resveratrol solution, whereas 41.68% drug still remained intact in a PAMAM G4-amine dendrimer (pH 7) formulation (FIG. 6—lower).

Example 5. Antioxidant Efficacy Evaluation of PAMAM-Resveratrol

DPPH Assay: Antioxidant efficacy was determined by a DPPH (1,1-diphenyl-2-picrylhydrazyl) assay, in which changes in color (from a deep violet to light yellow) were measured at 515 nm using a UV/visible light spectrophotometer. 1% PAMAM G4-Amine dendrimer (pH 7)-resveratrol complex was compared against the control of resveratrol in water alone. Measurements were taken at 0.25, 0.5, 1, 2, and 19 hours.

The DPPH assay showed pronounced, nearly instantaneous radical scavenging (antioxidant activity) from the addition of the PAMAM G4-amine dendrimer (pH 7), with the 1% PAMAM G4-amine dendrimer-resveratrol formulation registering 64.6% inhibition at 0.25 hours and gradually decreasing to 51.2% inhibition at 19 hours. The control formulation registered virtually no inhibition over the length of the analysis. This pattern indicates the stability of resveratrol within the drug-dendrimer complex architecture.

Example 6. Transdermal Permeation Study of PAMAM-Resveratrol

Transdermal permeation studies were conducted using Franz Diffusion Cells (FDC) and rat skin samples. The diffusion cells had a 5 mL receptor chamber and were manufactured by Permegear. The formulations examined were a 0.1% PAMAM-G4 amine dendrimer-resveratrol formulation, a 1% PAMAM-G4 amine dendrimer-resveratrol formulation, a PAMAM-G4 amine dendrimer-resveratrol nanosuspension, and a control of free resveratrol in water. For each formulation, the receptor chamber of the FDC was filled with 5 mL of a PBS (pH 7.4):methanol 90:10 mixture. Skin samples from (Dahl Salt Sensitive rats) were cut to size and placed at the interface of the donor and receptor chambers. 0.5 mL of the desired formulation was placed in the donor chamber and the FDC was stirred on a stir plate set to 6 (on an arbitrary 10-point scale). At various intervals over a 24-hour period 400 uL was removed from the receptor chamber by means of the sampling arm and analyzed by HPLC. The volume was replaced by an equal amount of fresh PBS:methanol mixture. After 24 hours, an aliquot was taken from the donor chamber and the skin was removed and resveratrol recovered by soaking skin in 2 mL methanol and sonicating for 10 minutes followed by filtration and HPLC analysis as discussed before.

Figure 7:
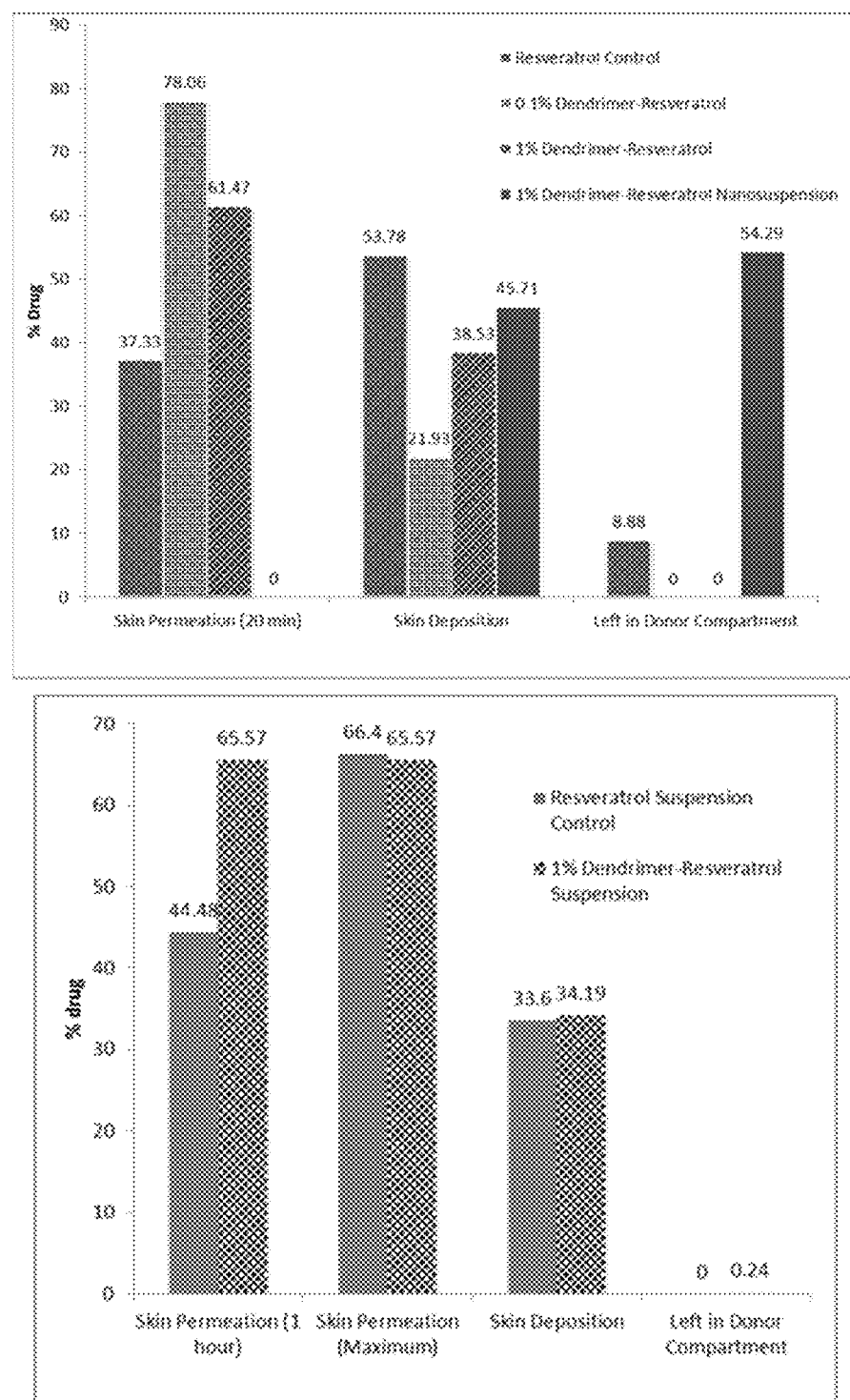
FIG. 7 is a series of graphs depicting the transdermal permeation of resveratrol in various PAMAM G4-amine dendrimer-resveratrol formulations.

The 0.1% PAMAM-G4 amine dendrimer-resveratrol showed 78.06% transdermal permeation compared to only 37.33% for resveratrol alone. Both the formulations depicted maximum transdermal permeation in 20 minutes. Significantly higher quantities of resveratrol were found in skin (53.78% vs. 21.9%) and the donor compartment (8.88% vs. 0%) for the neat resveratrol formulation compared to the dendrimer-resveratrol formulations (FIG. 7—upper). This clearly indicates that dendrimer promotes resveratrol transdermal permeation. Furthermore, no dendrimer peak was observed by HPLC in the receptor compartment. This indicated that dendrimer did not cross the skin but promoted the permeation of resveratrol across the skin.

Additional transdermal permeation studies were performed examining the dendrimer effects on a resveratrol suspension. For these studies, a 1% PAMAM G4-Amine dendrimer-resveratrol formulation was prepared according to modified Protocol 2 except that the formulation was not filtered through a 0.2 um filter prior to being added to the donor compartment, leaving a suspension. A control suspension was prepared in a similar manner, without filtration. These formulations were analyzed and compared according to the procedures described above.

FIG. 7 (lower) shows the results of the resveratrol suspension transdermal permeation study. This demonstrated that a suspension containing 1% PAMAM-G4 amine dendrimer-resveratrol complex had a greater rate of permeation than a control suspension not containing dendrimer.

Strat-M® membrane (EMD, Millipore) is a synthetic membrane-based model with diffusion characteristics well-correlated to human skin. Strat-M® membrane is used as a screening tool for transdermal diffusion studies in the development of cosmetic products. The preceding permeation studies were conducted using Strat-M® membranes. However, no permeation of resveratrol through the membrane was observed. This indicates that in the present disclosure, dendrimer may be imparting a new mechanism to permeate drug through the skin.

Example 7. Dissolution Studies

Figure 8:
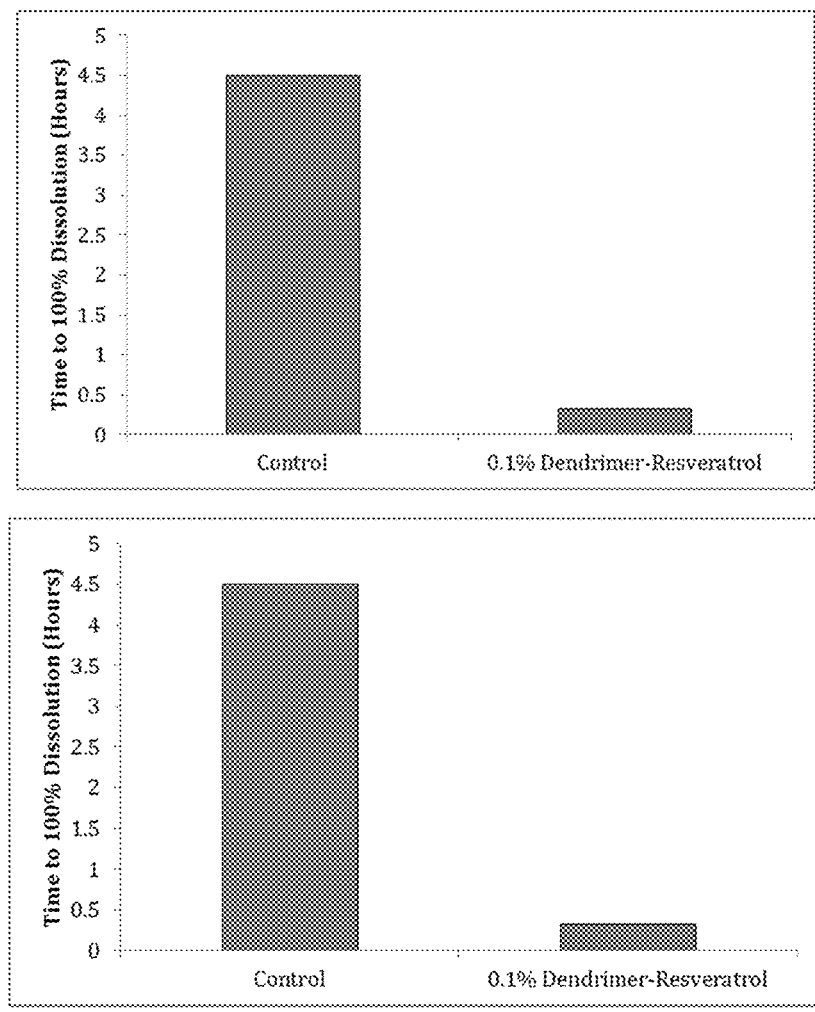
FIG. 8 is a series of graphs depicting the comparison of dissolution rates in simulated gastric fluid between a 0.1% PAMAM G4-amine dendrimer-resveratrol formulation and a control (upper); and the comparison of dissolution rates in simulated intestinal fluid between a 0.1% PAMAM G4-amine dendrimer-resveratrol formulation and a control (lower).

An examination was made regarding dissolution of resveratrol in simulated gastric and intestinal environments. 1 mL of a 0.1% PAMAM G4-Amine dendrimer-resveratrol formulation was prepared using Modified Protocol 2 and analyzed via HPLC. The formulation was split into 2 equal aliquots and lyophilized. Simulated gastric and intestinal fluids were prepared, with the simulated gastric fluid consisting of HCl, NaCl, Pepsin, and water while the simulated intestinal fluid consisted of NaOH, $KH_2PO_4$, and water. 10 mL of these simulated solutions were added to the lyophilized 0.1% PAMAM G4-Amine dendrimer-resveratrol formulation, and the fluids were stirred at a low speed (1 on an arbitrary 10-point scale stir plate). This experiment was protected from light. At various time points, 0.5 mL aliquots of fluid were removed from the chambers and analyzed via HPLC. The volume removed was replaced with fresh simulated fluid. Control formulations of resveratrol alone, were analyzed simultaneously and compared to the dendrimer-containing formulations In the dissolution studies, the 0.1% PAMAM G4-Amine dendrimer-resveratrol formulations dissolved far more rapidly than resveratrol alone in both simulated gastric and simulated intestinal fluid. The 0.1% dendrimer-resveratrol formulations reached 100% dissolution in 20 minutes in the simulated gastric (FIG. 8—upper) and simulated intestinal (FIG. 8—lower), while resveratrol alone was still dissolving at the final time point in the experiment, 4.5 hours.

Although the disclosure above has been described in terms of various aspects and specific embodiments, it is not so limited. A variety of suitable alterations and modifications for operation under specific conditions will be apparent to those skilled in the art. It is therefore intended that the following claims be interpreted as covering all such alterations and modifications as fall within the spirit and scope of the disclosure.

All patents, publications and references cited herein are hereby fully incorporated by reference. In case of conflict between the present disclosure and incorporated patents, publications and references, the present disclosure should control.

The invention claimed is:

1. A composition comprising a dendrimer-resveratrol complex, the composition being essentially free of organic solvent, wherein the dendrimer has pyrrolidinone surface groups.

2. The composition of claim 1, wherein the composition further comprises water.

3. The composition of claim 1, wherein the aqueous solubility of the resveratrol associated with the dendrimer is at least 10 times greater than the aqueous solubility of neat resveratrol, as measured at pH 7.

4. The composition of claim 1, wherein the aqueous solubility of the resveratrol associated with the dendrimer is at least 10 times greater than the aqueous solubility of neat resveratrol, as measured at pH 2.5.

5. The composition of claim 1, wherein the dendrimer is poly(amidoamine) (PAMAM), poly(propyleneimine) (PPI), poly(lysine), poly(glycerol) or a hyperbranched structure; wherein the hyperbranched structure is selected from the group consisting of dendrigrafts, polyesters, polyamides, and polyalcohols.

6. The composition of claim 1, wherein the dendrimer is a generation 4 PAMAM dendrimer having a diaminobutane core.

7. A pharmaceutical composition comprising a therapeutically effective amount of the composition of claim 1 and one or more pharmaceutically acceptable carriers.

8. The composition of claim 1, further comprising a retinoid, an antioxidant, or a combination thereof.

9. The composition of claim 8, wherein the antioxidant is selected from the group consisting of ascorbic acid and salts and esters thereof, epichlorocatechin, curcumin, tocopherol and salts and esters thereof, butylated hydroxyl benzoic acids and salts thereof, butylated hydroxytoluene, butylated hydroxyanisole, 6-hydroxy-2,5,7,8-tetramethylchroman-2-carboxylic acid, gallic acids and alkyl esters thereof, uric acid and salts and alkyl esters thereof, sorbic acid and salts thereof, amines, sulfhydryl compounds, sodium metabisulfite, dihydroxy fumaric acid and salts thereof, glutathione, and a combination thereof.

10. The composition of claim 8, wherein the retinoid is retinol.

11. A composition comprising a dendrimer-resveratrol complex and a retinoid, the composition being essentially free of organic solvent.

12. The composition of claim 11, wherein the composition further comprises water.

13. The composition of claim 11, wherein the aqueous solubility of the resveratrol associated with the dendrimer is at least 10 times greater than the aqueous solubility of neat resveratrol, as measured at pH 7.

14. The composition of claim 11, wherein the aqueous solubility of the resveratrol associated with the dendrimer is at least 10 times greater than the aqueous solubility of neat resveratrol, as measured at pH 2.5.

15. The composition of claim 11, wherein the dendrimer is poly(amidoamine) (PAMAM), poly(propyleneimine) (PPI), poly(lysine), poly(glycerol) or a hyperbranched structure; wherein the hyperbranched structure is selected from the group consisting of dendrigrafts, polyesters, polyamides, and polyalcohols.

16. The composition of claim 11, wherein the dendrimer is a generation 4 PAMAM dendrimer having a diaminobutane core and surface groups comprising amine surface groups, pyrrolidinone surface groups, or a combination thereof.

17. The composition of claim 11, wherein the retinoid is retinol.

18. The composition of claim 11, further comprising an antioxidant.

19. The composition of claim 18, wherein the antioxidant is selected from the group consisting of ascorbic acid and salts and esters thereof, epichlorocatechin, curcumin, tocopherol and salts and esters thereof, butylated hydroxyl benzoic acids and salts thereof, butylated hydroxytoluene, butylated hydroxyanisole, 6-hydroxy-2,5,7,8-tetramethylchroman-2-carboxylic acid, gallic acids and alkyl esters thereof, uric acid and salts and alkyl esters thereof, sorbic acid and salts thereof, amines, sulfhydryl compounds, sodium metabisulfite, dihydroxy fumaric acid and salts thereof, glutathione, and a combination thereof.

20. A pharmaceutical composition comprising a therapeutically effective amount of the composition of claim 8 and one or more pharmaceutically acceptable carriers.

21. A pharmaceutical composition comprising a therapeutically effective amount of the composition of claim 11 and one or more pharmaceutically acceptable carriers.

* * * * *